United States Patent
Chun

(10) Patent No.: US 8,058,032 B2
(45) Date of Patent: Nov. 15, 2011

(54) METHOD FOR AMPLIFYING UNKNOWN DNA SEQUENCE ADJACENT TO KNOWN SEQUENCE

(75) Inventor: Jong-Yoon Chun, Seoul (KR)

(73) Assignee: Seegene, Inc., Seoul (KR)

( * ) Notice: Subject to any disclaimer, the term of this patent is extended or adjusted under 35 U.S.C. 154(b) by 493 days.

(21) Appl. No.: 10/578,521

(22) PCT Filed: Nov. 10, 2003

(86) PCT No.: PCT/KR03/02407
§ 371 (c)(1),
(2), (4) Date: May 8, 2006

(87) PCT Pub. No.: WO2005/045073
PCT Pub. Date: May 19, 2005

(65) Prior Publication Data
US 2007/0172824 A1    Jul. 26, 2007

(51) Int. Cl.
C12P 19/34     (2006.01)
C07H 21/04     (2006.01)
C12Q 1/68      (2006.01)

(52) U.S. Cl. ................ 435/91.2; 435/6.12; 536/24.3

(58) Field of Classification Search ............ None
See application file for complete search history.

(56) References Cited

U.S. PATENT DOCUMENTS 4,683,195 A     7/1987  Mullis et al.
5,962,228 A *   10/1999 Brenner ............ 435/6

FOREIGN PATENT DOCUMENTS

WO    WO 01/94638         12/2001
WO    WO 03/050305        6/2003
WO    WO03/050305 A1 *    6/2003

OTHER PUBLICATIONS

Stone & Wharton (1994) Nucleic acids Research vol. 22, No. 13 pp. 2612 -2618.*
Welsh & McClelland (1990) Nucleic acids Research vol. 18, No. 24 pp. 7213-7218.*
Liu and Whittier (1995) Genomics 25, 674-681.*
Watanabe et al. 2001 Journal of Microbiological methods 44 : pp. 253-262.*
Oberste et al. J Clin. Microbiol. vol. 35 No. 5 May 1999 pp. 1288-1293.*
Hwang et al., "Annealing Control Primer System for Improving Specificity of PCR Amplification," BioTechniques 35:1180-1184, 2003.

* cited by examiner

Primary Examiner — Teresa E Strzelecka
Assistant Examiner — Suchira Pande
(74) Attorney, Agent, or Firm — Clark & Elbing LLP

(57) ABSTRACT

The present invention relates to a method for amplifying an unknown nucleotide sequence adjacent to a known nucleotide sequence, which comprises the step of (a) performing a primary amplification of said unknown nucleotide sequence using a DNA walking annealing control primer (DW-ACP) and a first target-specific primer; in which said step (a) comprises: (a-1) performing a first-stage amplification of said unknown nucleotide sequence at a first annealing temperature, comprising at least one cycle of primer annealing, primer extending and denaturing using a first degenerate DW-ACP containing a degenerate random nucleotide sequence to hybridize with said unknown nucleotide sequence and a hybridizing nucleotide sequence substantially complementary to a site on said unknown nucleotide sequence; and (a-2) performing a second-stage amplification at a second annealing temperature to render said first degenerate DW-ACP not to function as a primer.

27 Claims, 5 Drawing Sheets

METHOD FOR AMPLIFYING UNKNOWN DNA SEQUENCE ADJACENT TO KNOWN SEQUENCE

CROSS-REFERENCE TO RELATED APPLICATIONS

This application claims priority under 35 U.S.C. §371 from international application PCT/KR2003/002407, filed Nov. 10, 2003.

BACKGROUND OF THE INVENTION

1. Field of the Invention

The present invention relates to a method for amplifying an unknown nucleotide sequence adjacent to a known nucleotide sequence, in particular to a method for amplifying an unknown nucleotide sequence using a novel DNA walking annealing control primer and its applications.

2. Description of the Related Art

The polymerase chain reaction (PCR) presents the most effective method for selectively amplifying specific DNA fragments. In the PCR procedure, oligonucleotides complementary to the known 5' and 3' sequences flanking the target nucleic acid serve as "primers" and play a key role.

Application of PCR to isolate and analyze a particular DNA region requires knowledge of the. DNA sequences flanking the region of interest. This generally limits amplification to regions of known DNA sequence. In the absence of the necessary sequence information, PCR amplification of a target DNA fraction in a complex DNA population is likely to result in the amplification of non-target DNA.

Many PCR-based methods have been developed and modified to isolate an unknown DNA sequence that flanks regions of known sequences. They include, inverse PCR (Triglia et al., 1988), panhandle PCR (Shyamala et al., 1989; Jones and Winistorfer, 1997), vectorette PCR (Arnold et al., 1991), anchored PCR (Roux et al., 1990), AP-PCR (Dominguez et al., 1994; Trueba and Johnson, 1996), capture PCR (Lagerstrom et al., 1991), and adapter- or cassette-ligated PCR (Iwahana et al., 1994; Riley et al., 1990; Siebert et al., 1995; Willems, 1998; Kilstrup and Kristiansen, 2000).

However, these methods have limitations such as the need to digest the DNA with restriction enzymes, ligate the digested DNA with linkers or with double-stranded, partially double-stranded, or single-stranded oligonucleotide cassettes, and purify and/or subclone the products before sequencing. The need for multiple steps in these protocols makes them cumbersome and inefficient. Furthermore, in these methods, the common problem is high background and non-specific products due to non-specific binding of the vector, adaptor, cassette, or tail primers.

Therefore, the methodology was further improved to provide a biotin/streptavidin system to capture biotinylated fragments of interest before the nested PCR is carried out (Rosenthal and Jones, 1990; Mishra et al. 2002). This method show an improvement to reduce the noise and to allow the amplification of the flanking region of any known sequence but requires a complicated procedure of immobilized step and also a lot of cost.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

To be free from the shortcomings of the conventional technologies described above, the present inventor has intensively researched to develop approaches capable of fundamentally and completely removing the high background problems in the amplification of unknown sequence, and as a result found a novel method for amplifying an unknown sequence adjacent to a known sequence, which permits to amplify an unknown sequence in a much more reliable and convenient manner.

Accordingly, it is an object of this invention to provide a method for amplifying an unknown nucleotide sequence adjacent to a known nucleotide sequence.

It is another object of this invention to provide a DNA walking annealing control primer for amplifying an unknown nucleotide sequence.

It is still another object of this invention to provide a kit for amplifying an unknown nucleotide sequence.

It is further object of this invention to provide a use of the present method described above for a process involving nucleic acid amplification of an unknown nucleotide sequence adjacent to a known nucleotide sequence.

Other objects and advantages of the present invention will become apparent from the detailed description to follow taken in conjugation with the appended claims and drawings.

DETAILED DESCRIPTION OF THIS INVENTION

Figure 1A:
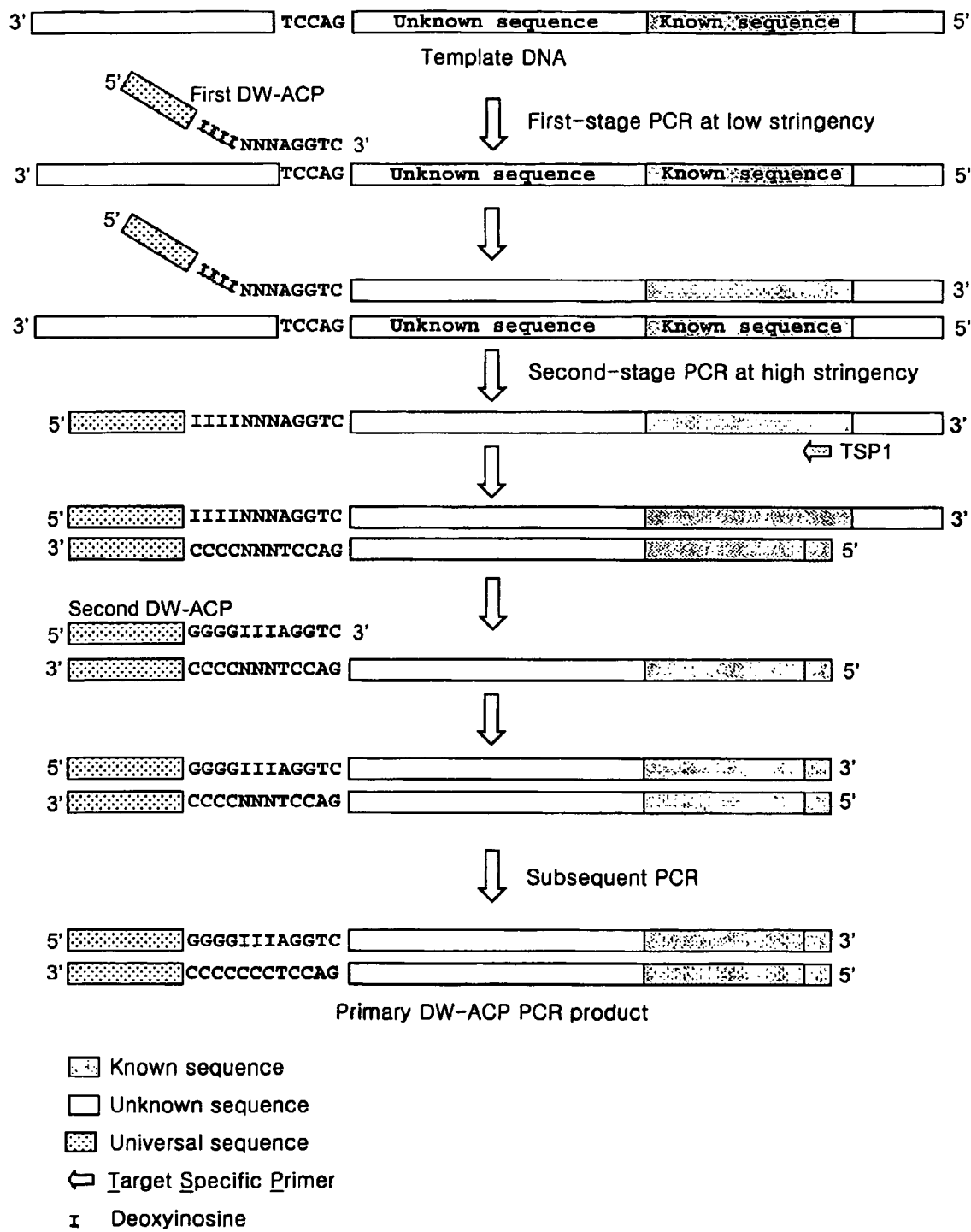
FIG. 1A shows a schematic representation of one specific embodiment of the primary amplification process using a first degenerate DNA walking annealing control primer (DW-ACP), a second DW-ACP and a first target-specific primer.
Figure 1B:
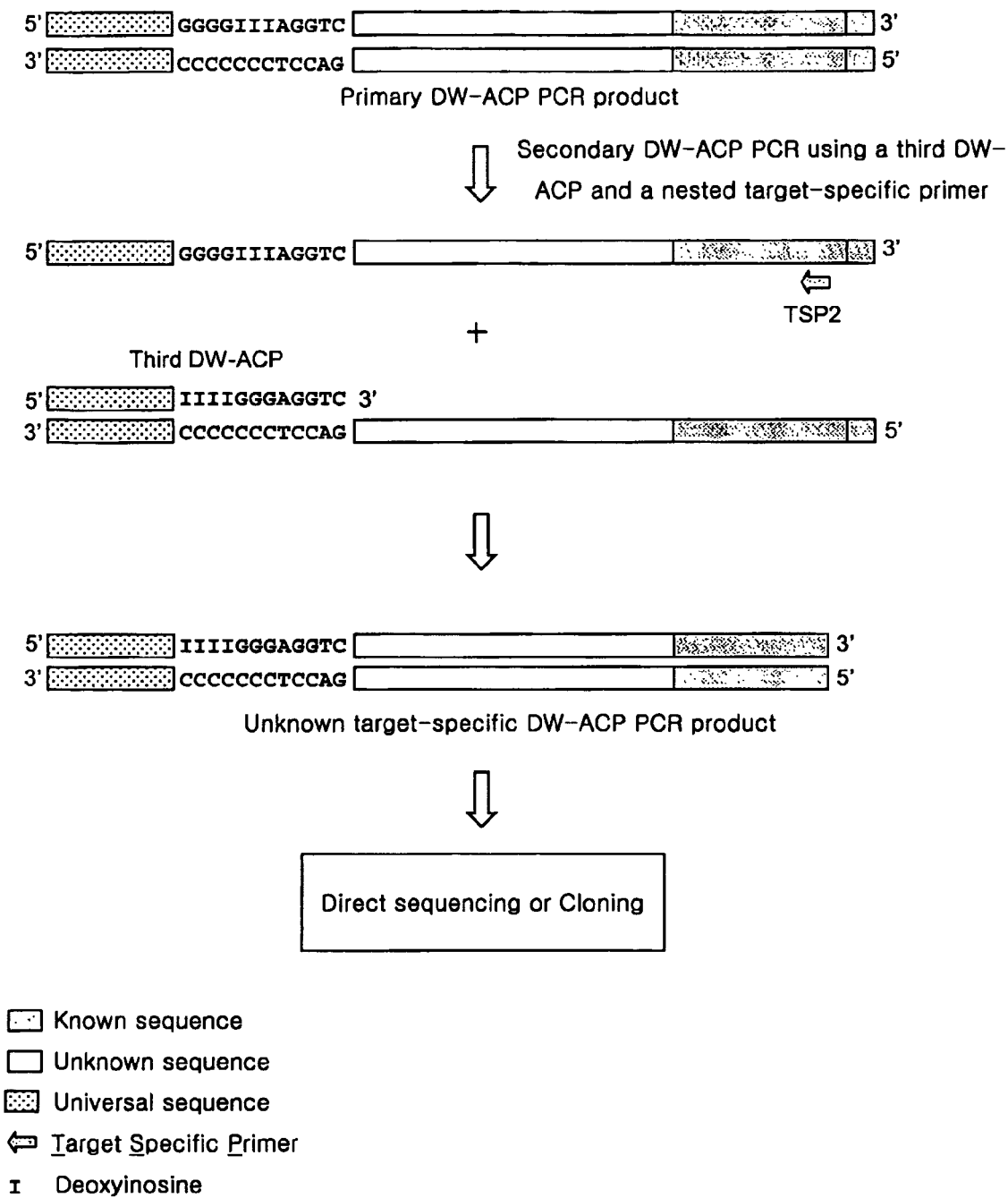
FIG. 1B schematically represents one specific embodiment of the secondary amplification process using a third DW-ACP and a second target-specific primer.

In one aspect of this invention, there is provided a method for amplifying an unknown nucleotide sequence adjacent to a known nucleotide sequence, which comprises the step of (a) performing a primary amplification of the unknown nucleotide sequence using a DNA walking annealing control primer (DW-ACP) and a first target-specific primer; in which the step (a) comprises: (a-1) performing a first-stage amplification of the unknown nucleotide sequence at a first annealing temperature, comprising at least one cycle of primer annealing, primer extending and denaturing using a first degenerate DW-ACP containing a degenerate random nucleotide sequence to hybridize with the unknown nucleotide sequence and a hybridizing nucleotide sequence substantially complementary to a site on the unknown nucleotide sequence, wherein the first annealing temperature enables the first degenerate DW-ACP to function as a primer, whereby a first degenerate DW-ACP extension product is generated; and (a-2) performing a second-stage amplification at a second annealing temperature to render the first degenerate DW-ACP not to function as a primer, comprising: (a-2-1) amplifying the first degenerate DW-ACP extension product using the first target-specific primer to hybridize with a target-specific nucleotide sequence substantially complementary to a site on the known nucleotide sequence, whereby a target-specific primer extension product is generated, (a-2-2) amplifying the target-specific primer extension product using a second DW-ACP to hybridize with a nucleotide sequence complementary to the first degenerate DW-ACP sequence of the target-specific primer extension product, whereby a second DW-ACP extension product is generated, and (a-2-3) amplifying the second DW-ACP extension product using the second DW-ACP and the first target-specific primer, whereby a primary amplification product without a degenerate random nucleotide sequence is generated.

The subject invention pertains to a unique method for selectively amplifying an unknown DNA sequence adjacent to regions of known sequences from a DNA or a mixture of nucleic acids using a novel DNA walking annealing control primer (hereinafter referred to as "DW-ACP").

To overcome the problems of the current DNA (or genome) walking methods including multiple and complicated steps and the inherent background of PCR-based methods, the Annealing Control Primer (ACP) system, which has been developed by the present inventor and disclosed in WO 03/050305, is modified to selectively amplify an unknown sequence adjacent to regions of known sequences. Since the ACP system is capable of dramatically improving amplification specificity, the use of ACP fundamentally prevents the non-specific priming of a primer during amplification and also simplifies the amplification process in this application.

According to a preferred embodiment, the first degenerate DW-ACP has a general formula I:

$$5'-X_p-Y_q-Z_r-Q_s-3' \qquad (I)$$

wherein, $X_p$ represents a 5'-end portion having a pre-selected nucleotide sequence, $Y_q$ represents a regulator portion comprising at least two universal base or non-discriminatory base analog residues, $Z_r$ represents a degenerate random sequence portion having a degenerated random nucleotide sequence, $Q_s$ represents a 3'-end portion having a hybridizing nucleotide sequence substantially complementary to a site on the unknown nucleotide sequence to hybridize therewith, p, q, r and s represent the number of nucleotides, and X, Y, Z and Q are deoxyribonucleotide or ribonucleotide.

The first degenerate DW-ACP of this invention has been developed for the amplification of an unknown nucleotide sequence adjacent to a known nucleotide sequence using and modifying the principles of annealing control primers developed by the present inventor and disclosed in WO 03/050305, the teachings of which are incorporated herein by reference in its entity.

The principle of the first degenerate DW-ACP is based on the composition of an oligonucleotide primer having 3'- and 5'-end distinct portions separated by a regulator portion comprising at least two universal base or non-discriminatory base analog residues and the effect of the regulator portion on the 3'- and 5'-end portions in the oligonucleotide primer. The presence of the regulator portion between the 3'- and 5'-end portions of the first degenerate DW-ACP acts as a main factor, which is responsible for the improvement of primer annealing specificity.

The term "nucleic acid" or "nucleotide" is a deoxyribonucleotide or ribonucleotide polymer in either single or double-stranded form, including known analogs of natural nucleotides unless otherwise indicated. Therefore, the first DW-ACP of this invention can be employed in nucleic acid amplification using a single or double-stranded gDNA, cDNA or mRNA as a template. The term "portion" used herein in conjunction with the primer of this invention refers to a nucleotide sequence separated by an intervening portion such as the regulator portion. The term "3'-end portion" or "5'-end portion" refers to a nucleotide sequence at the 3'-end or 5'-end of the primer of this invention, respectively, which is separated by the regulator portion.

The term "primer" as used herein refers to an oligonucleotide, whether occurring naturally or produced synthetically, which is capable of acting as a point of initiation of synthesis when placed under conditions in which synthesis of primer extension product which is complementary to a nucleic acid strand (template) is induced, i.e., in the presence of nucleotides and an agent for polymerization such as DNA polymerase and at a suitable temperature and pH. The primer is preferably single stranded for maximum efficiency in amplification. Preferably, the primer is an oligodeoxyribonucleotide. The primer of this invention can be comprised of naturally occurring dNMP (i.e., dAMP, dGMP, dCMP and dTMP), modified nucleotide or non-natural nucleotide.

The term "substantially complementary" in reference to primer is used herein to mean that the primer is sufficiently complementary to hybridize selectively to a nucleotide sequence under the designated annealing conditions, such that the annealed primer can be extended by polymerase to form a complementary copy of the nucleotide sequence. Therefore, this term has a different meaning from "perfectly complementary" or related terms thereof.

It has been widely known that nucleotides at some ambiguous positions of degenerate primers have been replaced by universal base or a non-discriminatory analogue such as deoxyinosine (Ohtsuka et al, 1985; Sakanari et al., 1989), 1-(2'-deoxy-beta-D-ribofuranosyl)-3-nitropyrrole (Nichols et al., 1994) and 5-nitroindole (Loakes and Brown, 1994) for solving the design problems associated with the degenerate primers because such universal bases are capable of non-specifically base pairing with all four conventional bases. However, there has not been any report that this universal base or a non-discriminatory analogue such as deoxyinosine, 1-(2'-deoxy-beta-D-ribofuranosyl)-3-nitropyrrole and 5-nitroindole can be applied to a primer for amplifying unknown nucleotide sequence, i.e., DNA walking primer, as a regulator to discriminate each functional portion of a primer in accordance with annealing temperature.

The term "universal base or non-discriminatory base analog" used herein refers to one capable of forming base pairs with each of the natural DNA/RNA bases with little discrimination between them.

According to a preferred embodiment, the universal base or non-discriminatory base analog in the regulator portion includes deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-0-methoxyethyl inosine, 2'0-methoxyethyl nebularine, 2'-0-methoxyethyl 5-nitroindole, 2'-0-methoxyethyl 4-nitro-benzimidazole, 2'-0-methoxyethyl 3-nitropyrrole and combinations thereof, but not limited to. More preferably, the universal base or non-discriminatory base analog is deoxyinosine, inosine, 1-(2'-deoxy-beta-D-ribofuranosyl)-3-nitropyrrole or 5-nitroindole, most preferably, deoxyinosine.

The presence of polydeoxynucleotides having universal bases such as deoxyinosines in a primer generates a low annealing temperature region due to its weaker hydrogen bonding interactions in base pairing. As an extension of this theory, the present inventor has induced that the presence of the polydeoxynucleotides having universal bases between the 5'-end portion and the degenerate sequence portion plus the 3'-end portion of a primer could generate a region which has a lower melting temperature, forms a boundary to each of the 5'-end portion and the degenerate sequence portion plus the 3'-end portion of the primer, and facilitates the annealing of the degenerate sequence portion plus the 3'-end portion to the target sequence at specific temperature. This theory provides the basis of the first degenerate DW-ACP of this invention.

The regulator portion in the first DW-ACP is capable of regulating an annealing portion (i.e., the degenerate random sequence and 3'-end portions) of the primer in association with annealing temperature. This regulator portion prevents annealing of the 5'-end portion sequence to a template and restricts the annealing portion of the primer to its degenerate sequence portion and 3'-end portion at the first annealing temperature. Consequently, the regulator portion dramatically improves annealing of the degenerate sequence portion plus the 3'-end portion of the first degenerate DW-ACP to the template.

In a preferred embodiment, the regulator portion of the first DW-ACP contains at least 3 universal bases or non-discriminatory base analog residues between the 5'-end portion and the degenerate sequence portion, more preferably, at least 4 universal bases or non-discriminatory base analogs. Advantageously, the universal base residues between the 5'-end portion and the degenerate sequence portion of the first degenerate DW-ACP can be up to 10 residues in length. According to one embodiment, the regulator portion of the first DW-ACP contains 2-10 universal base or non-discriminatory base analog residues. Most preferably, the universal bases between the 5'-end portion and the degenerate sequence portion of the first degenerate DW-ACP are about 3-5 residues in length. The presence of universal bases or non-discriminatory base analog residues may be contiguous or intermittent, preferably, contiguous.

The 5'-end portion of the first degenerate DW-ACP contributes partially to improve the annealing specificity. Importantly, the 5'-end portion serves alone or with other portions as a priming site in subsequent amplifications after the first round of amplification. According to a preferred embodiment, the pre-selected nucleotide sequence of the 5'-end portion is substantially not complementary to any site on the template nucleic acid.

Generally, the 5'-end portion of the first degenerate DW-ACP contains at least 10 nucleotides in length. Preferably, the 5'-end portion sequence can be up to 60 nucleotides in length. More preferably, the 5'-end portion sequence is from 6 to 50 nucleotides, most preferably, from 18 to 25 nucleotides in length. Using a longer sequence at the 5'-end portion may reduce the efficiency of the first degenerate DW-ACP, but a shorter sequence may reduce the efficiency of annealing under high stringent conditions.

In some embodiment, the pre-selected nucleotide sequence of the 5'-end portion of the first degenerate DW-ACP can be composed of a universal primer sequence such as T3 promoter sequence, T7 promoter sequence, SP6 promoter sequence, and M13 forward or reverse universal sequence.

According to one embodiment of the present invention, some modifications in the 5'-end portion of the first degenerate DW-ACP can be made unless the modifications abolish the advantages of the DW-ACP, i.e., improvement in annealing specificity. For example, the 5'-end portion can comprises a sequence or sequences recognized by a restriction endonuclease(s), which makes it feasible to clone the amplified product into a suitable vector. In addition, the 5'-end portion can comprises at least one nucleotide with a label for detection or isolation of amplified product. Suitable labels include, but not limited to, fluorophores, chromophores, chemiluminescers, magnetic particles, radioisotopes, mass labels, electron dense particles, enzymes, cofactors, substrates for enzymes and haptens having specific binding partners, e.g., an antibody, streptavidin, biotin, digoxigenin and chelating group. The 5'-end portion also comprises bacteriophage RNA polymerase promoter region.

The degenerate random sequence portion of the first degenerate DW-ACP is present between the regulator and 3'-end portions. The term "degenerate random sequence" portion refers to a nucleotide sequence in which each nucleotide can be occupied by any one of the four deoxyribonucleotides, i.e., dATP, dTTP, dCTP, and dGTP. Thus, the degenerate random sequence portion provides a pool of primers with various nucleotide sequences, at least one of which will be anticipated to anneal to a site on an unknown target sequence of a template. For example, if the first degenerate DW-ACP comprising three degenerate nucleotides at the degenerate random sequence portion is synthesized, sixty-four distinct oligonucleotides are produced. Consequently, the use of a degenerate random sequence portion provides the first degenerate DW-ACP with more probability to hybridize to the unspecified target nucleic acid. When the target core sequence of the first degenerate DW-ACP including the degenerate sequence and 3'-end portion sequence hybridizes to a site of a template, there are several complementary binding sites of the degenerate portion and 3'-end portion sequence of the first DW-ACP present on the unknown target sequence of the template. Interestingly, the present inventor has observed that one major target product is usually generated by which the first degenerate DW-ACP binds to a target-binding site which is the nearest distance from the target-specific primer sequence of the known sequence. It may suggest that the primers being hybridized on the other binding sites, which are present on more distance from the target-specific primer sequence, are not favorable to generate any product because the extension of the primer hybridized with the nearest binding site from the target-specific primer sequence may bother the extension of the primers hybridized on the other binding sites.

The length of the degenerate random sequence portion of the first DW-ACP may be determined based on various considerable factors such as the length of the 3'-end portion, the amplification yield and the length of nucleotides to be amplified. For example, if the length of the degenerate sequence portion becomes longer, the amplification yield becomes lower in the present method. Generally, the length of the degenerate sequence portion ranges from 1 to 5, preferably 2-5, more preferably, 2-4, most preferably, 3.

The 3'-end portion of the first degenerate DW-ACP has a nucleotide sequence substantially complementary to a site on an unknown nucleotide sequence. It will be appreciated that the 3'-end portion of the first degenerate DW-ACP can have one or more mismatches to a site on the unknown nucleotide sequence to an extent that the first degenerate DW-ACP can serve as a primer. Most preferably, the 3'-end portion of the first DW-ACP has a nucleotide sequence perfectly complementary to a site on the unknown nucleotide sequence, i.e., no mismatches.

The 3'-end portion of the first degenerate DW-ACP has a nucleotide sequence to hybridize with a site on the unknown sequence, which is so-called "arbitrary" nucleotide sequence. The term "arbitrary nucleotide sequence" is used herein to mean the nucleotide sequence that is chosen without knowledge of the sequence of the unknown nucleic acids to be amplified.

Generally, the 3'-end portion of the first degenerate DW-ACP is at least 3 nucleotides in length. It is important that the annealing portion (i.e., the degenerate sequence and 3'-end portions) of the first degenerate DW-ACP is at least 6 nucleotides in length, which is considered the minimal requirement of length for primer annealing with specificity. Practically, the primer annealing with specificity could be promising with at least 8 nucleotides in the annealing portion. Preferably, the 3'-end portion sequence is from 3 to 20 nucleotides in length, more preferably, 3-10 nucleotides, and most preferably, 4-6 nucleotides.

The 3'-end portion of the first degenerate DW-ACP is prepared to have a specific arbitrary nucleotide sequence. The specific arbitrary nucleotide sequence may contain the Kozak sequence of mRNA including the translation initiation codon ATG, such as 5'-ANNATGN-3', where N is any one of the four deoxynucleotides (McBratney and Samow, 1996). The specific arbitrary nucleotide sequence may also contain the canonical polyadenylation signal sequence AATAAA (Juretic and Theus, 1991). Alternatively, the nucleotide at the 5'-end of the 3'-end portion of the first degenerate DW-ACP may be varied to have one of four deoxyribonucleotides, so that four types of the first degenerate DW-ACP are obtained in terms of the nucleotide sequence of the 3'-end portion.

The length of the 3'-end portion of the first degenerate DW-ACP may be determined based on various considerable factors such as the length of nucleotides to be amplified, the length of the degenerate sequence portion, and the amplification yield. For example, if the 3'-end portion has 4 arbitrary nucleotides in length, theoretically the four-base sequence combination can exist once in every 256 bp in the template. Thus, the length of nucleotides to be amplified will be more than 256 bp.

The entire first DW-ACP is preferably from 20 to 80 nucleotides in length, more preferably, 28-50 nucleotides, and most preferably, 3040 nucleotides.

In the present method, the first target-specific primer substantially complementary to a site on the known nucleotide sequence of a template is used. The term "substantially complementary" in reference to the first target-specific primer has the same meaning as that for the first DW-ACP.

The primary amplification in the present invention is conducted by a two-stage amplification under different annealing temperature to maximize the advantages of the DW-ACP system.

The methods of the present invention can be used to amplify any desired nucleic acid molecule. Such molecules may be either DNA or RNA. The molecule may be in either a double-stranded or single-stranded form, preferably, double-stranded. Where the nucleic acid as starting material is double-stranded, it is preferred to render the two strands into a single-stranded, or partially single-stranded, form. Methods known to separate strands includes, but not limited to, heating, alkali, formamide, urea and glycoxal treatment, enzymatic methods (e.g., helicase action) and binding proteins. For instance, the strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a MRNA is employed as starting material for amplification, a reverse transcription step is necessary prior to amplification, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al., *Nucleic Acids Res.* 16:10366 (1988)). For reverse transcription, an oligonucleotide dT primer hybridizable to poly A tail of mRNA is used. Reverse transcription can be done with a reverse transcriptase.

The present methods do not require that the molecules to be amplified have any particular sequence or length. In particular, the molecules which may be amplified include any naturally occurring procaryotic, eucaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleotide sequence can also be any nucleic acid molecule which has been or can be chemically synthesized. Thus, the nucleotide sequence may or may not be found in nature.

The first degenerate DW-ACP used in the present invention is hybridized or annealed to a site on the unknown nucleotide sequence so that a double-stranded structure is formed. Conditions of nucleic acid hybridization suitable for forming such double stranded structures are described by Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985). The sequence of the annealing portion (i.e., the degenerate sequence and 3'-end portions) of the first DW-ACP needs not to exhibit precise complementarity, but need only to be substantially complementary in sequence to be able to form a stable double-stranded structure. Thus, departures from complete complementarity are permissible, so long as such departures are not sufficient to completely preclude hybridization to form a double-stranded structure. Hybridization of the first DW-ACP to a site on the unknown sequence is a prerequisite for its template-dependent polymerization with polymerases. Factors (see Joseph Sambrook, et al., *Molecular Cloning, A Laboratory Manual*, Cold Spring Harbor Laboratory Press, Cold Spring Harbor, N.Y. (2001); and Haymes, B. D., et. al.,

*Nucleic Acid Hybridization, A Practical Approach*, IRL Press, Washington, D.C. (1985)) which affect the base pairing of the first DW-ACP to its complementary nucleic acids subsequently affect priming efficiency. The nucleotide composition of the first degenerate DW-ACP can affect the temperature at which annealing is optimal and therefore can affect its priming efficiency.

A variety of DNA polymerases can be used in the amplification step of the present methods, which includes "Klenow" fragment of *E. coli* DNA polymerase I, a thermostable DNA polymerase and bacteriophage T7 DNA polymerase. Preferably, the polymerase is a thermostable DNA polymerase such as may be obtained from a variety of bacterial species, including *Thermus aquaticus* (Taq), *Thermus thermophilus* (Tth), *Thermus fliformis, Thermis flavus, Thermococcus literalis*, and *Pyrococcusfuriosus* (Pfu). When a polymerization reaction is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired.

All of the enzymes used in this amplification reaction may be active under the reaction conditions. Indeed, buffers exist in which all enzymes are near their optimal reaction conditions.

Two amplification stages of the present method are separated only in time. The first-stage amplification should be followed by the second-stage amplification. Therefore, the two-stage amplification can be conducted in a reaction including all types of primers, the first DW-ACP, the second DW-ACP and the first target-specific primer.

Annealing or hybridization in the two-stage amplification is performed under stringent conditions that allow for specific binding between a nucleotide sequence and the primers. Such stringent conditions for annealing will be sequence-dependent and varied depending on environmental parameters. In the present methods, it is preferred that two amplification stages are carried out under different conditions, inter alia, at different annealing temperature each other. Preferably, the annealing in the first-stage amplification is performed under low stringent condition, inter alia, at low annealing temperature. More preferably, the first annealing temperature is between about 35° C. and 50° C., and most preferably, 40-48° C. At the first annealing temperature, the annealing portion of the first DW-ACP is restricted to the degenerate sequence and 3'-end portions, thereby improving annealing specificity.

According to the present method, the first-stage amplification under low stringent conditions is carried out for at least one cycle of annealing, extending and denaturing to improve the specificity of primer annealing during the first-stage amplification, and through the subsequent cycles, the second-stage amplification is processed more effectively under high stringent conditions. It is most preferred that the first-stage amplification is carried out for one cycle. One cycling of the first-stage amplification is critical because it could fundamentally prevent the first degenerate DW-ACP alone from generating non-specific amplification products. During the one cycle of the primary amplification (first-stage amplification), the 3'-end portion of the first DW-ACP binds to the unknown target sites of the template under such low stringent conditions. However, during the next cycles of the primary amplification (second-stage amplification), the 3' end portion of the first DW-ACP no longer plays as a primer to bind to the template or the extended primer sequence under such high stringent conditions, except to a nucleotide sequence complementary to the first DW-ACP. Eventually, the first degenerate DW-ACP alone cannot make any product during the primary amplification (see FIG. 2) except for the first degenerate DW-ACP extension product.

The second-stage amplification is preferably performed under high stringent condition, inter alia, at high annealing temperature. Advantageously, the second annealing temperature is between about 50° C. and 72° C., more preferably, 50-65° C., and most preferably, 52-65° C. At a high annealing temperature such as the second annealing temperature, the first degenerate DW-ACP no longer serves as a primer; instead, the second DW-ACP and the first target-specific primer work as a primer with higher specificity.

The second-stage amplification under high stringent conditions is carried out for at least one cycle, preferably, at least 5 cycles to generate unknown target-specific products without degenerate random nucleotide sequence derived from the first degenerate DW-ACP, using the combination of the second DW-ACP and the first target-specific primer. In a more preferred embodiment, the second-stage amplification is carried out for 10-40 cycles, more preferably, 10-30 cycles, and most preferably, 10-20 cycles.

High and low stringent conditions may be readily determined from the standard known in the art. "Cycle" refers to the process which results in the production of a copy of target nucleic acid. A cycle includes a denaturing step, an annealing step, and an extending step.

In the most preferable embodiment, the amplification is performed in accordance with PCR which is disclosed in U.S. Pat. Nos. 4,683,195, 4,683,202, and 4,800,159.

According to a preferred embodiment, the second DW-ACP has a general formula II:

$$5'\text{-}X'_p\text{-}S_u\text{-}Y'_v\text{-}Z'_w\text{-}3' \tag{II}$$

wherein, $X'_p$ represents a 5'-end portion having a nucleotide sequence corresponding to the 5'-end portion of the first degenerate DW-ACP, $S_u$ represents a supplementary annealing portion comprising a nucleotide sequence to hybridize with a portion opposite to the regulator portion of the first degenerate DW-ACP in the target-specific primer extension product of the step (a-2-1), $Y'_v$ represents a regulator portion comprising at least two universal base or non-discriminatory base analog residues and prevents annealing of the $X'_p$ and $S_u$ portions to non-target sequences except to the nucleotide sequence complementary to the first degenerate DW-ACP, $Z'_w$ represents a 3'-end portion having a nucleotide sequence corresponding to the 3'-end portion of the first degenerate DW-ACP, p, u, v and w represent the number of nucleotides, and X', S, Y', and Z' are deoxyribonucleotide or ribonucleotide.

The term "corresponding to" used herein with reference to two related nucleotide sequences is intended to express both perfectly and partially identical sequences to an extent that the one nucleotide sequence can be hybridized with a nucleotide sequence hybridizable with the other comparative nucleotide sequence.

The second DW-ACP of the formula II has a nucleotide sequence corresponding to that of the first degenerate DW-ACP. The primer of the formula II exhibits much higher annealing specificity.

The 5'-end portion of the second DW-ACP has a nucleotide sequence corresponding to the 5'-end portion of the first DW-ACP. That is, the nucleotide sequence of the 5'-end portion of the second DW-ACP may be completely identical or partially identical to that of the 5'-end of the first DW-ACP. Departures from complete identity are permissible, so long as such departures are not sufficient to completely preclude hybridization to form a double-stranded structure between the 5'-end portion of the second DW-ACP and the nucleotide sequence with the opposite sense to the 5'-end portion of the first DW-ACP.

The supplementary annealing portion ($S_u$) is very unique in the second DW-ACP of the formula II, which is partially responsible for the complete removal of the high background problem resulting from the non-specific binding of primer to non-specific sites. The supplementary annealing portion comprises a nucleotide sequence to hybridize with a portion opposite to the regulator portion of the first degenerate DW-ACP. This strategy for designing the supplementary annealing portion employs the recognition of universal base by DNA polymerase (e.g., Taq polymerase) to direct the incorporation of natural dNMPs. The recognition of universal base by DNA polymerase has been reported by Geoffrey C. Hoops, et al. (*Nucleic Acids Research,* 25(24):4866-4871 (1997)), which is incorporated herein by reference. For example, 8-hydroxyguanine, 2-hydroxyadenine, 6-O-methylguanine and xanthine direct the incorporation of (C and A), (T and A), (T and C) and (T and C), respectively. Furthermore, Geoffrey C. Hoops, et al have resulted that a base having nitropyrrole and inosine direct most preferably the incorporation of dAMP and dCMP, respectively.

Therefore, if the regulator portion of the first degenerate DW-ACP comprises at least two deoxyinosine or inosine residues, the supplementary annealing portion should comprise at least 2 deoxyguanosine nucleotides because deoxycytidine nucleotides are most preferably incorporated into the portion opposite to the regulator portion by Taq polymerase.

In the second DW-ACP, $Y'_v$, a regulator portion, prevents annealing of the $X'_p$ and $S_u$ portions to non-target sequences except to the sequence complementary to the first DW-ACP. Furthermore, the regulator portion provides an additional annealing portion by way of the indiscriminative binding of universal bases or non-discriminatory base analogs such that the second DW-ACP is able to selectively anneal to the sequences complementary to the first degenerate DW-ACP sequences in the resultant products.

The regulator portion of the formula II is hybridized with a portion opposite to the degenerate sequence portion of the first degenerate DW-ACP. The universal base or non-discriminatory base analog suitable in regulator portion may include any base to show loss of discrimination when participating in DNA replication known in the art. Preferably, the universal base or non-discriminatory base analog includes deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-0-methoxyethyl inosine, 2'0-methoxyethyl nebularine, 2'-0-methoxyethyl 5-nitroindole, 2'-0-methoxyethyl 4-nitro-benzimidazole, 2'-0-methoxyethyl 3-nitropyrrole, 8-hydroxyguanine, 2-hydroxyadenine, 6-O-methylguanine, xanthine, $O^2$-ethylthymidine, $O^4$-ethylthymidine, 2-amino-6-methoxyaminopurine, 6H,8H-3,4-dihydropyrimido[4,5-c][1,2]oxazin-7-one, $N^6$-methoxyadenine and combinations thereof. More preferably, the universal base or non-discriminatory base analog is deoxyinosine, inosine, 1-(2'-deoxy-beta-D-ribofuranosyl)-3-nitropyrrole or 5-nitroindole, most preferably, deoxyinosine.

The length of the regulator portion of the formula II is mainly determined by that of the degenerate sequence portion of the first degenerate DW-ACP. Furthermore, if the nucleotide at the 5'-end of the 3'-end portion of the first degenerate DW-ACP is designed to have a specific nucleotide from four deoxyribonucleotides, the regulator portion is longer by 1 nucleotide. The universal bases in the regulator portion of the formula II exist preferably in a contiguous arrangement.

The 3'-end portion in the second DW-ACP has a nucleotide sequence corresponding to the 3'-end portion of the first degenerate DW-ACP. The nucleotide sequence of the 3'-end portion of the second DW-ACP may be completely or partially identical to that of the 3'-end of the first DW-ACP. Departures from complete identity are permissible, so long as such departures are not sufficient to completely preclude hybridization to form a double-stranded structure between the 3'-end portion of the second DW-ACP and the nucleotide sequence with the opposite sense to the 3'-end portion of the first DW-ACP. Most preferably, the nucleotide sequence of the 3'-end portion of the second DW-ACP is completely identical to that of the 3'-end of the first DW-ACP because the perfect match of the 3'-end portion of the primer to template is required for a successful amplification.

According to the second-stage amplification, the first target specific primer is annealed to its complementary sequence on the known nucleotide sequence to generate a target-specific primer extension product. If the regulator portion of the first degenerate DW-ACP comprises universal bases or non-discriminatory base analogs, its opposite strand on the target-specific primer extension product comprises the nucleotides preferably recognized by DNA polymerase as described hereinabove. For example, where the regulator portion of the first degenerate DW-ACP comprises at least two deoxyinosine or inosine residues, at least 2 deoxycytidine nucleotides are incorporated into its opposite strand on the target-specific primer extension product.

Following the generation of the target-specific primer extension product, the primary amplification product is generated using the second DW-ACP and the first target-specific primer. During the second-stage amplification, all portions of the second DW-ACP are involved in annealing exclusively to a nucleotide sequence complementary to the first DW-ACP sequence present at the 3'-end of the amplification product, but not able to anneal to any other site due to the effect of the regulator. Accordingly, the second DW-ACP alone cannot make any non-specific product (see FIG. 2).

The final primary amplification product having no the degenerate random sequence derived from the first DW-ACP is used as a template for a secondary amplification. Where the secondary amplification is followed by the primary amplification, the elimination of degenerate random sequence on the primary amplification product ensures the secondary amplification to perform with more specificity and reliability, which is discussed hereunder.

According to a preferred embodiment, the present method further comprises the step of (c) performing a secondary amplification at a third annealing temperature, comprising at least one cycle of primer annealing, primer extending and denaturing, using a third DW-ACP comprising at its 3'-end portion a nucleotide sequence to hybridize with the opposite-sense nucleotide sequence to the second DW-ACP sequence present at the 3'-end of the primary amplification product and the first target-specific primer of the step (a) or a nested target-specific primer designed to amplify an internal region of the primary amplification product.

The secondary amplification preferably follows a nested amplification process known in the art for selectively amplifying an unknown target product from the primary amplification products. The secondary amplification is preferably performed under a high stringent condition, inter alia, at high annealing temperature. Advantageously, the high annealing temperature is between about 50° C. and 72° C., more preferably, 50-70° C., and most preferably, 55-68° C. At a high annealing temperature, all portions, not a portion, of the third DW-ACP are involved in annealing. Therefore, the third DW-ACP is able to anneal exclusively to a nucleotide sequence complementary to the second DW-ACP. The secondary amplification under high stringent conditions is carried out for at least one cycle, preferably, at least 5 cycles to amplify the primary amplification product. In a more preferred embodiment, the secondary amplification is carried out for 10-40 cycles.

In the most preferable embodiment, the secondary amplification is performed in accordance with PCR which is disclosed in U.S. Pat. Nos. 4,683,195, 4,683,202 and 4,800,159.

According to a preferred embodiment, the third DW-ACP has a general formula III:

$$5'-X''_p-Y''_q-C_c-3' \quad \quad \quad (III)$$

wherein, $X''_p$ represents a 5'-end portion having a nucleotide sequence corresponding to all or a part of the 5'-end portion of the second DW-ACP, $Y''_q$ represents a regulator portion comprising at least two universal base or non-discriminatory base analog residues corresponding to the supplementary annealing portion, a part of the 5'-end portion, a part of supplementary annealing portion plus a part of the 5'-end portion, or a part of supplementary annealing portion plus a part of the regulator portion of the second DW-ACP of the formula II and prevents annealing of the $X''_p$ portion to non-target sequences of the primary amplification product except to the nucleotide sequence complementary to the second DW-ACP, $C_c$ represents a 3'-end portion having a nucleotide sequence to hybridize with the opposite-sense nucleotide sequence to all or a part of the 3'-end portion and regulator portion sequences of the second DW-ACP, p, q and c represent the number of nucleotides, and X'', Y'', and C are deoxyribonucleotide or ribonucleotide.

In the third DW-ACP, $X''_p$ preferably has a nucleotide sequence corresponding to all parts of the 5'-end portion of the second DW-ACP.

$Y''_q$ provides a binding portion to the opposite-sense nucleotide sequence to the second DW-ACP of the formula II as well as a regulatory portion that prevents annealing of the $X''_p$ portion to non-target sequences of the primary amplification product except to the nucleotide sequence complementary to the second DW-ACP. In addition to this, it is surprising that the regulator portion intervening between two annealing portions, $X''_p$ and $C_c$ can provide two portions present on both sides with highly annealing specificity.

The 3'-end portion, $C^c$ has a nucleotide sequence to hybridize with the opposite-sense nucleotide sequence to the regulator portion sequences of the second DW-ACP. Therefore, if the regulator portion of the second DW-ACP comprises at least two deoxyinosine or inosine residues, the 3'-end portion should comprise at least 2 deoxyguanosine nucleotides because deoxycytidine nucleotides are most preferably incorporated into the portion opposite to the regulator portion, as described previously.

The descriptions for the second DW-ACP can be applied to the third DW-ACP of the formula III.

According to a preferred embodiment, the present method further comprises the step (b) of purifying the primary amplification product of the step (a) to remove the first and second DW-ACPs and the first target-specific primer. For example, the purification of amplified product can be accomplished by gel electrophoresis, column chromatography, affinity chromatography or hybridization. It is most preferable that the purification be carried out using a spin column with silica-gel membrane. This method employs the selective binding properties of a silica-gel membrane to which the amplified products are adsorbed in the presence of high salt, while contaminants such as primer pass through the column. Therefore, the amplified products are quickly purified and obtained from the amplification reactions.

According to more preferred embodiment, the present method comprises the primary amplification of step (a) comprising the two-stage amplification and the secondary amplification of step (c). Most preferably, the present method comprises the primary amplification of step (a) comprising the two-stage amplification, the purification of step (b) and the secondary amplification of step (c).

Where the desired results to completely overcome non-specific amplification is not accomplished or is doubtable, or where the amplified products of step (c) were not visible on agarose gels, the nested amplification may be further performed for at least I cycle with another target-specific primer designed to amplify an internal region of the secondary amplification product.

The present method may be combined with many other processes known in the art to achieve a specific aim. For example, the isolation (or purification) of amplified product may follow the primary or secondary amplification. This can be accomplished by gel electrophoresis, column chromatography, affinity chromatography or hybridization. In addition, the amplified product of this invention may be inserted into suitable vehicle for cloning. Furthermore, the amplified product of this invention may be expressed in suitable host harboring expression vector. In order to express the amplified product, one would prepare an expression vector that carries the amplified product under the control of, or operatively linked to a promoter. Many standard techniques are available to construct expression vectors containing the amplified product and transcriptional/translational/control sequences in order to achieve protein or peptide expression in a variety of host-expression systems. The promoter used for procaryotic host includes, but not limited to, pLλ promoter, trp promoter, lac promoter and T7 promoter. The promoter used for eucaryotic host includes, but not limited to, metallothionein promoter, adenovirus late promoter, vaccinia virus 7.5K promoter and the promoters derived from polyoma, adenovirus 2, simian virus 40 and cytomegalo virus. Certain examples of procaryotic hosts are *E. coli, Bacillus subtilis*, and other enterobacteriaceae such as *Salmonella typhimurium, Serratia marcescens*, and various *Pseudomonas* species. In addition to microorganisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, tobacco mosaic virus) or transformed with recombinant plasmid expression vectors (e.g., Ti plasmid) containing one or more coding sequences. The expressed polypeptide from the amplified product may be generally purified with a variety of purposes in accordance with the method known in the art.

In another aspect of this invention, there is provided a DNA walking annealing control primer for amplifying an unknown nucleotide sequence adjacent to a known nucleotide sequence, which is represented by the following general formula I:

$$5'\text{-}X_p\text{-}Y_q\text{-}Z_r\text{-}Q_s\text{-}3' \quad \text{(I)}$$

wherein, $X'_p$ represents a 5'-end portion having a pre-selected nucleotide sequence, $Y_q$ represents a regulator portion comprising at least two universal base or non-discriminatory base analog residues, $Z_r$ represents a degenerate random sequence portion having a degenerated random nucleotide sequence, $Q_s$ represents a 3'-end portion having a hybridizing nucleotide sequence substantially complementary to a site on the unknown nucleotide sequence to hybridize therewith, p, q, r and s represent the number of nucleotides, and X, Y, Z and Q are deoxyribonucleotide or ribonucleotide.

In still another aspect of this invention, there is provided a DNA walking annealing control primer for amplifying an unknown nucleotide sequence adjacent to a known nucleotide sequence, which is represented by the following general formula II:

$$5'\text{-}X'_p\text{-}S_u\text{-}Y'_v\text{-}Z'_w\text{-}3' \quad \text{(II)}$$

wherein, $X'_p$ represents a 5'-end portion having a nucleotide sequence corresponding to the 5'-end portion of the first degenerate DW-ACP, $S_u$ represents a supplementary annealing portion comprising a nucleotide sequence to hybridize with a portion opposite to the regulator portion of the first degenerate DW-ACP in the target-specific primer extension product of the step (a-2-1), $Y'_v$ represents a regulator portion comprising at least two universal base or non-discriminatory base analog residues and prevents annealing of the $X'_p$ and $S_u$ portions to non-target sequences of the amplified product of the step (a) except to the nucleotide sequence complementary to the first degenerate DW-ACP, $Z'_w$ represents a 3'-end portion having a nucleotide sequence corresponding to the 3'-end portion of the first degenerate DW-ACP, p, u, v and w represent the number of nucleotides, and X', S, Y', and Z' are deoxyribonucleotide or ribonucleotide.

In further aspect of this invention, there is provided a DNA walking annealing control primer for amplifying an unknown nucleotide sequence adjacent to a known nucleotide sequence, which is represented by the following general formula III:

$$5'\text{-}X''_p\text{-}Y_q\text{-}C_c\text{-}3' \quad \text{(III)}$$

wherein, $X''_p$ represents a 5'-end portion having a nucleotide sequence corresponding to all or a part of the 5'-end portion of the second DW-ACP, $Y''_q$ represents a regulator portion comprising at least two universal base or non-discriminatory base analog residues corresponding to the supplementary annealing portion, a part of the 5'-end portion, a part of supplementary annealing portion plus a part of the 5'-end portion, or a part of supplementary annealing portion plus a part of the regulator portion of the second DW-ACP of the formula II and prevents annealing of the $X''_p$ portion to non-target sequences of the primary amplification product except to the nucleotide sequence complementary to the second DW-ACP, $C_c$ represents a 3'-end portion having a nucleotide sequence to hybridize with the opposite-sense nucleotide sequence to all or a part of the 3'-end portion and regulator portion sequences of the second DW-ACP, p, q and c represent the number of nucleotides, and X", Y", and C are deoxyribonucleotide or ribonucleotide.

Since the DW-ACP of this invention is employed in the amplification process of this invention described above, the common descriptions between them are omitted in order to avoid the complexity of this specification leading to undue multiplicity.

In still further aspect of this invention, there is provided a kit for amplifying an unknown nucleotide sequence adjacent to a known nucleotide sequence, which comprises the first degenerate DNA walking annealing control primer, the second DNA walking annealing control primer, the third DNA walking annealing control primer, or combinations thereof.

According a preferred embodiment, the present kit may further comprise target-specific primers. The present kits may optionally include the reagents required for performing DNA amplification such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. Optimal amounts of reagents to be used in a given reaction can be readily determined by the skilled artisan having the benefit of the current disclosure. The kits, typically, are adapted to contain in separate packaging or compartments the constituents afore-described.

The subject invention can provide an improved method for selectively amplifying an unknown nucleotide sequence from a nucleic acid or a mixture of nucleic acids (DNA or mRNA) by performing nucleic acid amplifications, preferably, PCR.

In another aspect of this invention, there is provided a use of the present method described previously for a process involving nucleic acid amplification of unknown nucleotide sequence adjacent to a known nucleotide sequence.

The present invention can be applied to a variety of nucleic acid amplification-based technologies. Representative examples are:

(i) genome walking for obtaining series of unknown DNA regions on either side of chromosomal regions of known nucleotide sequence. Examples are genome sequencing projects, cloning of promoter region, identification of gene structure such as exon/intron junction, gap filling, and location or orientation of transgene;

(ii) rapid amplification of 5'- and 3'-Ends of cDNA (RACE) for cloning or sequencing full-length cDNA of cDNA or for splicing analysis;

(iii) mapping of regions containing deletions, insertions, and translocations; and (iV) rapid amplification of BAC ends without shotgun cloning for whole genome sequencing.

The following specific examples are intended to be illustrative of the invention and should not be construed as limiting the scope of the invention as defined by appended claims.

EXAMPLES

In the experimental disclosure which follows, the following abbreviations apply: M (molar), mM (millimolar), μM (micromolar), g (grams), μg (micrograms), ng (nanograms), l (liter), ml (milliliters), μl (microliters), ° C. (degree Centigrade), Roche (Roche Diagnostics, Mannheim, Germany), Promega (Promega Co., Madison, USA), QIAGEN (QIAGEN GmbH, Hilden, Germany), and Applied Biosystems (Foster City, Calif., USA).

The oligonucleotide sequences used in the Examples are shown in Sequence Listing.

Example 1

Evaluation of ACP System in DNA Walking ACP-PCR Method

The effect of the ACP system in DNA walking ACP-PCR was evaluated by comparing ACP system with conventional longer primer system. Plant genomic DNA was used as a template.

A. Primer Design

DNA walking annealing control primers (DW-ACPs) were designed for amplifying an unknown sequences adjacent to regions of any known sequences from a DNA or a mixture of nucleic acids of any organism. The first DW-ACP was in a tripartite structure having a polydeoxyinosine [poly(dI)] linker between the 3'-end target binding sequence and the 5'-end non-target tail sequence, wherein the 3'-end target binding sequence comprises a predetermined arbitrary sequence at the 3'-end and a degenerate random sequence at the 5'-end, and one of nucleotides A, C, T and G between the 3'- and 5'-ends of the 3'-end target binding sequence. Therefore, at least four different DW-ACP primers will be generated depending on the arbitrary sequence at the 3'-end of the 3'-end target binding sequence of the DW-ACP.

Four different degenerate first DNA walking annealing control primers (first DW-ACPs), wherein the annealing control primer (ACP) has been developed by the present inventor and disclosed in WO 03/050305, were designed as follows:

```
DW-ACP1-A:
5'-TCACAGAAGTATGCCAAGCGAIIIINNNAGGT    (SEQ ID NO:
                                         1)
C-3';

DW-ACP1-C:
5'-TCACAGAAGTATGCCAAGCGAIIIINNNCGGT    (SEQ ID NO:
                                         2)
C-3';

DW-ACP1-T:
5'-TCACAGAAGTATGCCAAGCGAIIIINNNTGGT    (SEQ ID NO:
                                         3)
C-3';
and DW-ACP1-G:
5'-TCACAGAAGTATGCCAAGCGAIIIINNNGGGT    (SEQ ID NO:
                                         4)
C-3'.
```

Second DNA walking annealing control primers (second DW-ACPs) were designed as follow:

```
DW-ACP2-N:
5'-TCACAGAAGTATGCCAAGCGAGGGGIIIIGGT    (SEQ ID NO:
                                         5)
C-3';

DW-ACP2-NA:
5'-TCACAGAAGTATGCCAAGCGAGGGGIIIAGGT    (SEQ ID NO:
                                         6)
```

```
C-3';

DW-ACP2-NC:
5'-TCACAGAAGTATGCCAAGCGAGGGGIIICGGT    (SEQ ID NO:
                                         7)
C-3';

DW-ACP2-NT:
5'-TCACAGAAGTATGCCAAGCGAGGGGIIITGGT    (SEQ ID NO:
                                         8)
C-3';
and DW-ACP2-NG:
5'-TCACAGAAGTATGCCAAGCGAGGGGIIIGGGT    (SEQ ID NO:
                                         9)
C-3'.
```

Third DNA walking annealing control primers (third DW-ACPs) were designed as follows:

```
DW-ACP3-N1:
5'-TCACAGAAGTATGCCAAGCGAIIIIGGGGGGT    (SEQ ID NO: 10)
C-3';

DW-ACP3-N2:
5'-TCACAGAAGTATGCCAAGCGAGIIIIGGGGGT    (SEQ ID NO: 11)
C-3';
and

DW-ACP3-N3:
5'-TCACAGAAGTATGCCAAGCGAGGIIIIGGGGT    (SEQ ID NO: 12)
C-3'.
```

Another third DW-ACP was also designed as a nested primer to be used in a nested DW-ACP PCR and the sequence is as follow:

```
Nested DW-P3-N:
5'-CCAAGCGAGGGGGGGGGGTC-3'.    (SEQ ID NO: 13)
```

The sequence of the second DW-ACP was designed to exclusively anneal to the sequences completely complementary to all of the pool of the degenerate first DW-ACP, not any other non-target sites of a template due to the feature of ACP structure. The third DW-ACP including the nested DW-ACP is used in the nested amplification.

The polydeoxyinosine [poly(dI)] linker of ACP prevents annealing of the 5' end tail sequence to the non-target site of the template and facilitates primer hybridization at the 3' end to the target sequence at specific temperature, resulting in a dramatic improvement of annealing specificity (Hwang et al., 2003).

As controls, conventional DNA walking longer primers (DW-Ps) having a tail sequence without the polydeoxyinosine [poly(dI)] linker were used and their sequences are as follows:

```
DW-P1-A:
5'-TCACAGAAGTATGCCAAGCGANNNAGGTC-3';    (SEQ ID NO: 14)

DW-P1-C:
5'-TCACAGAAGTATGCCAAGCGANNNCGGTC-3';    (SEQ ID NO: 15)
```

-continued

DW-P1-T:
5'-TCACAGAAGTATGCCAAGCGANNNTGGTC-3'; (SEQ ID NO: 16)

DW-P1-G:
5'-TCACAGAAGTATGCCAAGCGANNNGGGTC-3'; (SEQ ID NO: 17)
and

DW-P1:
5'-TCACAGAAGTATGCCAAGCGANNNNGGTC-3'. (SEQ ID NO: 18)

The tail primers, JYC3 and JYC3-ACP, which correspond to the 5'-end portion sequences of the DW-ACPs and DW-Ps, are as follows:

JYC3: 5'-TCACAGAAGTATGCCAAGCGA-3'. (SEQ ID NO: 19)

The primers described herein were synthesized by means of a DNA synthesizer (Expedite 8900 Nucleic Acid Synthesis System, Applied Biosystems (ABI)) according to a standard protocol. The deoxyinosine in the primers was incorporated using deoxyinosine CE phosphoramidite (ABI). The primers were purified by means of an OPC cartridge (ABI), and their concentrations were determined by Lw spectrophotometry at 260 nm. In the primers described above, "I" symbolizes deoxyinosine and "N" symbolizes a degenerate nucleotide occupied by any one of the four deoxyribonucleotides, i.e., dATP, dCTP, dTTP, and dGTP.

B. Genomic DNA Isolation

The soybean shoots were used to isolate genomic DNA. The samples were frozen quickly in liquid nitrogen and grinded. Two hundred micrograms of grinded samples were added to a 15 ml tube containing 1.2 ml of digestion buffer (100 mM NaCl, 10 mM Tris-Cl pH 8.0, 25 mM EDTA pH 8.0, and 0.5% SDS) and 6 µl of 20 mg/ml proteinase K. The tube was heated at 50° C. for 12 hr. The genomic DNA was extracted twice with an equal volume of phenol/chloroform/isoamyl alcohol (25:24:1) and once with chloroform/isoamyl alcohol (24:1). The genomic DNA was used as a template for evaluating the effect of ACP system in DNA walking ACP-PCR method.

C. Primary DNA Walking PCR

Current genome walking methods have high background problems due to non-specific priming of DNA walking (DW) primer to templates during PCR. Thus, DNA walling PCR was conducted using conventional DW-P alone or DW-ACP alone to determine whether the DW primers alone can make non-specific products.

Conventional PCR for the DW-P was conducted without target-specific primer in a final volume of 50 µl containing 100 ng of the soybean genomic DNA, 5 µl of 10×PCR reaction buffer (Roche), 4 µl of dNTP (2.5 mM each dATP, dCTP, dGTP, dTTP), 5 µl of DW-P1 (10 µM) or DW-P1-C (10 µM), and 0.5 µl of Taq polymerase (5 units/µl; Roche); the tube containing the reaction mixture was placed in a preheated (94° C.) thermal cycler; the PCR reactions consist of denaturing 94° C. for 5 min, followed by 30 cycles of 94° C. for 40 sec, 47° C. for 40 sec and 72° C. for 60 sec, and followed by a 5 min final extension at 72° C.

ACP-PCR for the first DW-ACP was conducted by a two-stage PCR amplification to maximize the advantage of ACP system.

The two-stage PCR amplification was conducted without a target-specific primer at two different annealing temperatures in a final volume of 50 µl containing 100 ng of the soybean genomic DNA, 5 µl of 10×PCR reaction buffer (Roche), 4 µl of dNTP (2.5 mM each DATP, dCTP, dGTP, dTTP), 1 µl of DW-ACP1-C (10 µM), and 0.5 µl of Taq polymerase (5 units/µl; Roche); the tube containing the reaction mixture was placed in a preheated (94° C.) thermal cycler; the first-stage PCR reaction consists of one cycle of 94° C. for 5 min, 45° C. for 3 min, and 72° C. for 1 min, followed by the second stage-PCR reaction by 30 cycles of 94° C. for 40 sec, 60° C. for 40 sec, and 72° C. for 60 sec, and followed by a 5 min final extension at 72° C.

D. Purification of Primary DNA Walking Products

To remove primers such as the DW-Ps or the first DW-ACPs used in the primary DNA walking PCR, the primary amplification products were purified using a spin column (PCR purification Kit, QIAGEN).

E. Secondary Amplification of the Primary DNA Walking PCR Products

To amplify the degenerate DNA walking products, PCR was conducted using the tail primer (JYC3) which corresponds to the 5'-end portion sequences of the DW-P or first DW-ACP, or the second DW-ACP which exclusively anneals to the sequences completely complementary to all of the pool of the degenerate first DW-ACP. The PCR amplification was conducted without a target-specific primer in a final volume of 50 µl containing 2 µl of the resultant PCR products generated by the DNA walking PCR, 5 µl of 10×PCR reaction buffer (Roche), 4 µl of dNTP (2.5 mM each dATP, dCTP, dGTP, dTTP), 1 µl of the tail primer, JYC3 (10 µM) or DW-ACP2-N (10 µM), and 0.5 µl of Taq polymerase (5 units/µl; Roche); the tube containing the reaction mixture was placed in a preheated (94° C.) thermal cycler; the PCR reactions consist of denaturing 94° C. for 5 min, followed by 30 cycles of 94° C. for 40 sec, 60° C. for 40 sec, and 72° C. for 60 sec, and followed by a 5 min final extension at 72° C.

F. Electrophoresis

The amplified products were analyzed by electrophoresis on a 2% agarose gel and detected by staining with ethidium bromide.

Figure 2:
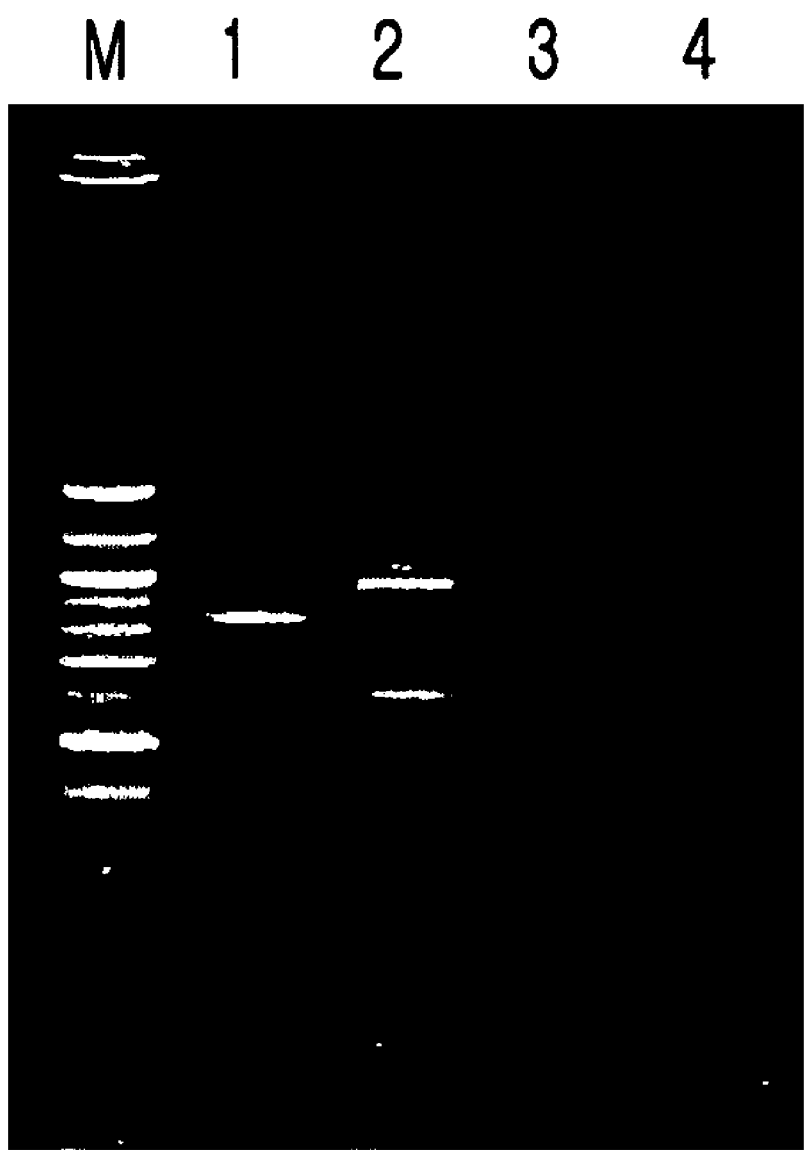
FIG. 2 shows the amplified products generated by DNA walking amplification. The conventional DNA walking primers alone generated amplification products (lanes 1 and 2). In contract, the DW-ACP alone generated no any visible products (lane 4) but if a tail primer was used, it generated a non-specific product due to non-specific binding of the tail primer to the template (lane 3).

FIG. 2 shows the amplified products generated by DNA walking PCR using a conventional DW primer or DW-ACP alone. The combination of the conventional DW primer, DW-P1 (lane 1) or DW-P1-C (lane 2), and JYC3 generated many PCR products although a target-specific primer was not used, indicating that the conventional DW primer and tail primer make non-specific products. The combination of the DW-ACP1-C and JYC3 generated a PCR product (lane 3) in spite of no use of a target-specific primer, while the combination of DW-ACP1-C and DW-ACP2-N did not generate any visible products (lane 4). These results indicate that although the first DW-ACP is used in the primary DNA walking ACP-PCR, if the tail primer, JYC3, is used in the secondary PCR amplification, it may bind to non-specific site of the template depending on the organism sources, resulting in the amplification of a non-specific product (lane 3). In contrast, if the DW-ACP2-N is used in the secondary PCR amplification, it cannot bind to any non-specific sites of the template due to the feature of ACP system, resulting in no product (lane 4).

Three major conclusions can be drawn on the basis of these results: 1) the conventional DW primer generates many non-specific products during the primary amplification due to the non-specific priming of the DW primer to the template and the generated products are amplified by the tail primer during the secondary amplification; 2) in contrast, the first DW-ACP binds to the specific sites of the template during the one cycle of the primary amplification (first-stage PCR) under such low stringent conditions, but no longer plays as a primer during the next cycles of the primary amplification (second-stage PCR) under such high stringent conditions that the annealing portion (i.e., the degenerate sequence and 3'-end portions) of the primer cannot bind to the template or the first DW-ACP primer extension products, and thus the second DW-ACP alone cannot make any product during the secondary PCR amplification; and 3) if a tail primer is used during the secondary PCR, the tail primer may bind to non-specific sites of the template, resulting in non-specific products.

The results of FIG. 2 indicate that DNA walking ACP-PCR system fundamentally eliminate the background problems, which are the major bottleneck of the current related technologies utilizing as primer tailing sequences, adaptor sequences or cassette sequences.

Example 2

Amplification of Promoter Sequences of the TNF-α Gene From Mouse Genome Using DNA Walking ACP PCR Method To demonstrate the application of the DNA walking ACP-PCR method of the subject invention, the promoter sequence of the mouse TNF-α gene was amplified from mouse genome using the TNF-α cDNA sequence information.

A. Primer Design

The same DW-ACPs designed in Example 1 were used in DNA walking ACP-PCR amplifications. Target-specific primers of the mouse TNF-α gene were designed as follows:

```
mTNFα-C1:
5'-CACCTTGCCCTGCCCATTAG-3';        (SEQ ID NO: 20)

mTNFα-C2:
5'-CCCTCACACTGTCCTTCTTGCC-3';      (SEQ ID NO: 21)

mTNFα-C3:
5'-GAATAAGGGTTGCCCAGACACTC-3';     (SEQ ID NO: 22)
and mTNFα-C4:
5'-GGAGTGCCTCTTCTGCCAGTTC-3'.      (SEQ ID NO: 23)
```

The primers described herein were synthesized by means of a DNA synthesizer as described in Example 1.

B. Genomic DNA Isolation

The mouse placenta tissues were used to isolate genomic DNA, as described in Example 1.

C. Primary DNA Walking ACP PCR

A primary DNA walking ACP PCR was conducted into four individual tubes, one each for each first DW-ACP, by a two-stage PCR amplification to maximize the advantage of ACP system, wherein the ACP system has been developed by the present inventor and disclosed in WO 03/050305.

The two-stage PCR amplification was conducted at two different annealing temperatures in a final volume of 50 μl containing 100 ng of the mouse genomic DNA, 5 μl of 10×PCR reaction buffer (Roche), 4 μl of dNTP (2.5 mM each DATP, dCTP, dGTP, dTTP), 1 μl of one of the first DW-ACPs (10 μM), 1 μl of second DW-ACP, DW-ACP2-N (10 μM), 1 μl of first target-specific primer, mTNFα-C1 (10 μM), and 0.5 μl of Taq polymerase (5 units/μl; Roche); the tube containing the reaction mixture was placed in a preheated (94° C.) thermal cycler; the first-stage PCR reaction consists of one cycle of 94° C. for 5 min, 40-45° C. for 1 min, and 72° C. for 2 min, followed by the second stage-PCR reaction by 10-30 cycles of 94° C. for 40 sec, 55-60° C. for 40 sec, and 72° C. for 60 sec, and followed by a 5 min final extension at 72° C.

D. Purification of Primary DNA Walking ACP PCR Products

To remove primers such as the first DW-ACPs and first target-specific primer used in the primary DNA walking ACP PCR, the primary amplification products were purified using a spin column (PCR purification Kit, QIAGEN).

E. Secondary DNA Walking ACP PCR

To amplify only an unknown target-specific product from the primary DNA walking ACP-PCR products that might have non-specific products due to the non-specific priming of the gene-specific primer, mTNFa-C1, to the template, a secondary DW-ACP PCR was conducted using the third DW-ACP and a nested TNF-α gene-specific primer designed to amplify an internal region of the primary amplification product. The secondary PCR amplification was conducted in a final volume of 50 μl containing 1-5 μl of the primary PCR amplification products, 5 μl of 10×PCR reaction buffer (Roche), 4 μl of dNTP (2.5 mM each dATP, dCTP, dGTP, dTTP), 1 μl of the third DW-ACP, DW-ACP3-N (10 μM), 1 μl of the nested gene-specific primer, mTNFa-C2 (10 μM), and 0.5 μl of Taq polymerase (5 units/μl; Roche); the tube containing the reaction mixture was placed in a preheated (94° C.) thermal cycler; the PCR reactions consist of denaturing 94° C. for 5 min, followed by 20-35 cycles of 94° C. for 40 sec, 55-60° C. for 40 sec, and 72° C. for 60 sec, and followed by a 5 min final extension at 72° C.

If the secondary amplification products were not visible on agarose gels, the thirdly amplification was further performed using another nested target-specific primer designed to amplify an internal region of the secondary amplification product with the third DW-ACP. The thirdly amplification was conducted in a final volume of 50 μl containing 1-2 μl of the secondary amplification products, 5 μl of 10×PCR reaction buffer (Roche), 5 μl of 25 mM $MgCl_2$, 4 μl of dNTP (2 mM each dATP, dCTP, dGTP, dTTP), 1 μl of the third DW-ACP, DW-ACP3-N1 (10 μM), 1 μl of the nested gene-specific primer, mTNFa-C3 (10 μM), and 0.5 μl of Taq polymerase (5 units/μl; Roche); the tube containing the reaction mixture was placed in a preheated (94° C.) thermal cycler; the PCR reactions consist of denaturing 94° C. for 5 min, followed by 30-35 cycles of 94° C. for 40 sec, 60-65° C. for 40 sec, and 72° C. followed by a 5 min final extension at 72° C.

F. Gel Extraction

The amplified products were analyzed by electrophoresis on a 2% agarose gel and detected by staining with ethidium bromide. The resulting PCR products can be also detected on a denaturing polyacrylamide gel by autoradiography or non-radioactive detection methods. After electrophoresis on agarose gel stained with EtBr, each PCR product was extracted using GENECLEAN II Kit (Q-BIOgene, USA).

G. Cloning or Sequencing

The extracted fragments were cloned into the pGEM-T Easy vector (Promega, USA) as described by the manufacturer. The plasmids were transformed to the XL1-blue competent cell. The transformed cells were plated on LB/ampicillin agar plates. The plasmids were isolated from single and white colonies. The inserts were confirmed by digestion with EcoR1 restriction enzyme. The plasmid with the insert was sequenced using ABI PRISM 310 genetic analyzer (Applied Biosystems, USA). Alternatively, the extracted fragments were used as templates for direct sequencing by the ABI PRISM 310 Genetic Analyzer (Perkin-Elmer Corp., Norwalk, Conn.) using Big dye Terminator cycle sequencing kit (Perkin-Elmer Corp.). Computer-assistant sequence analysis was carried out using the GeneRunner program (Hastings, Inc.).

Figure 3:
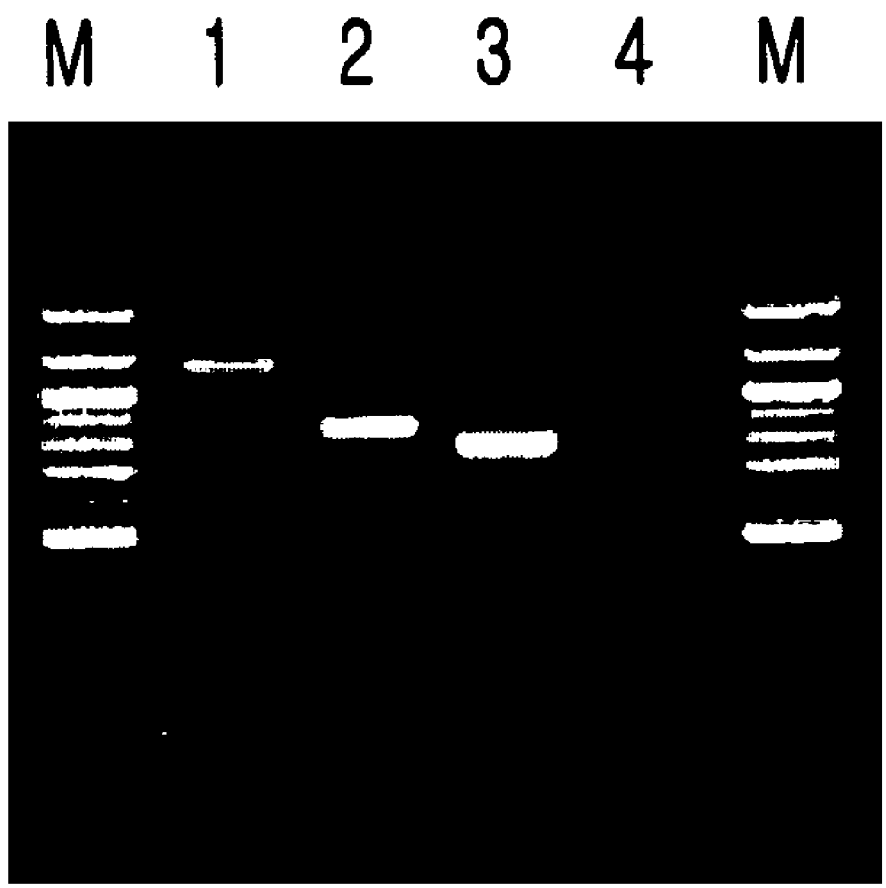
FIG. 3 shows the amplified products generated by DW-ACP-amplification for the amplification of promoter sequences of TNF-α gene. One major product with a different size was generated by each different first DW-ACPs, DW-ACP-A (lane 1), DW-ACP-T (lane 2), DW-ACP-G (lane 3), and DW-ACP-C (lane 4). These products were turned out to be the promoter sequences of TNF-α gene by sequence analysis.

FIG. 3 shows the amplified products generated by DNA walking ACP PCR for the amplification of promoter sequences of TNF-α gene. One major product with a different size was generated by each different first DW-ACPs, DW-ACP1-A (lane 1), DW-ACP1-T (lane 2), DW-ACP1-G (lane 3), and DW-ACP1-C (lane 4). These products were turned out to be the promoter sequences of TNF-α gene by sequence analysis. These results indicate that the DNA walking ACP PCR method of the subject invention can be applied to amplify an unknown genomic sequence that flanks regions of any known sequences from that genomic source.

Example 3

Amplification of the 5'-End Region Sequences of the PBP cDNA Using DNA Walking ACP PCR Method Although the full-length cDNA sequence of mouse presenilin-binding protein (PBP) is known, the DNA walking technology of the subject invention was further applied to amplify the 5'-end region sequence of PBP CDNA using only its' 3'-end region sequence information.

A. Primer Design

The same DW-ACPs used in Example 2 were used for DNA walking ACP PCR. Target-specific primers of the mouse PBP gene were designed based on its' 3'-end region sequence information as follows:

```
mPBP-C1:
5'-TCCACACCTTGAAGTCAAAGTC-3';      (SEQ ID NO: 24)

mPBP-C2:
5'-CAGAGGACAGGTACTGGACAGTAG-3';    (SEQ ID NO: 25)
and mPBP-C3:
5'-CAGTCTCATCACCATCCAGTCTC-3'.     (SEQ ID NO: 26)
```

B. First-Strand cDNA Synthesis

Total RNAs from the brain tissues of mouse strain ICR were isolated and used for the synthesis of first-strand cDNAs by reverse transcriptase, as described previously (Hwang et al., 2000). Reverse transcription reaction was performed using the total RNAs for 1.5 hr at 42° C. in a reaction volume of 20 µl composed of the following: 3 µg of total RNA, 4 µl of 5× reaction buffer (Promega, USA), 5 µl of dNTPs (each 2 mM), 2 µl of 10 µM cDNA synthesis primer (dT$_{20}$ or random hexamer), 0.5 µl of RNase inhibitor (40 units/µl, Promega), and 1 µl of reverse transcriptase (200 units/µl, Promega). First-strand cDNAs were diluted by adding 80 µl of ultra-purified H$_2$O.

The cDNA synthesis primer sequences are as follows:

```
dT20:    5'-TTTTTTTTTTTTTTTTTTTT-3';  (SEQ ID NO: 27)
and

N6:      5'-NNNNNN-3';                (SEQ ID NO: 28)
```

C. Primary DNA Walking ACP PCR

A primary DNA walking ACP PCR was conducted into four individual tubes, one each for each first DW-ACP, as described in Example 2, except the first target-specific primer, mPBP-C1.

D. Purification of Primary DNA Walking ACP PCR Products

To remove primers such as the first DW-ACPs and the first target-specific primer used in the DNA walking ACP-PCR, the primary PCR products were purified using a spin column (PCR purification Kit, QIAGEN). The purified primary amplification products can be diluted to 1-10 fold depending on the results of the primary amplification to be used as a template for the following secondary amplification.

E. Secondary DNA Walking ACP PCR

To amplify only an unknown target-specific product from the primary DNA walking ACP-PCR products that might have non-specific products due to the non-specific priming of the gene-specific primer, mPBP-C1, to the template, a secondary DW-ACP PCR was conducted using the third DW-ACP and a nested PBP gene-specific primer designed to amplify an internal region of the primary amplification product. The secondary PCR conditions were the same as the process E of Example 2, except the nested target-specific primer, mPBP-C2.

If the secondary amplification products were not visible on agarose gels, the thirdly amplification was further performed using another nested target-specific primer designed to amplify an internal region of the secondary amplification product with the third DW-ACP. The secondary amplification products can be diluted to 1-1,000 fold depending on the results of the secondary amplification to be used as a template for the following thirdly amplification. The thirdly amplification PCR conditions were the same as the above secondary ACP PCR, except the nested target-specific primer, mPBP-C3.

F. Gel Extraction

The amplified products were analyzed as described in the Gel extraction (Process F) of Example 2.

G. Cloning or Sequencing

The extracted fragments were cloned or directly sequenced as described in the Cloning or Sequencing (Process G) of Example 2.

Figure 4:
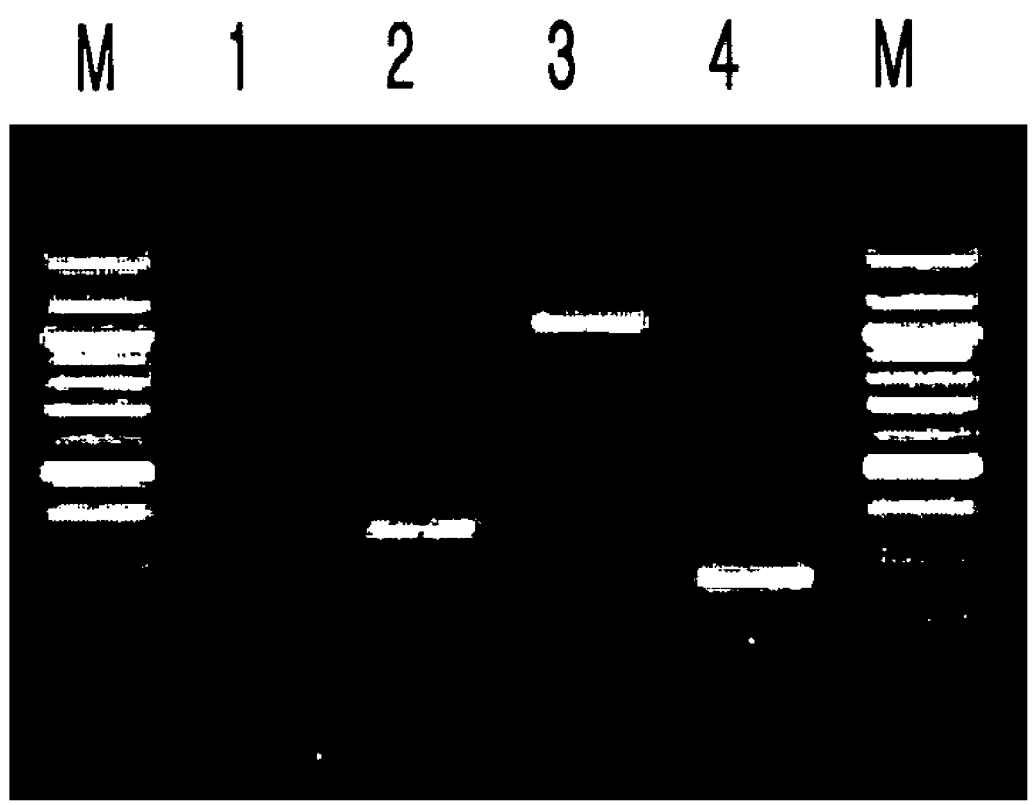
FIG. 4 shows the amplified products generated by DW-ACP-amplification for the amplification of the 5'-end region sequences of PBP cDNA. One major product with a different size was generated by each different first DW-ACPs, DW-ACP-A (lane 1), DW-ACP-T (lane 2), DW-ACP-G (lane 3), and DW-ACP-C (lane 4). These products were turned out to be the 5'-end region sequences of PBP cDNA by sequence analysis.

FIG. 4 shows the amplified products generated by DNA walking ACP PCR for the amplification of the 5'-end region sequences of PBP cDNA. One major product with a different size was generated by each different first DW-ACPs, DW-ACP1-A (lane 1), DW-ACP1-T (lane 2), DW-ACP1-G (lane 3), and DW-ACP1-C (lane 4). These products were turned out to be the 5'-end region sequences of PBP cDNA by sequence analysis. These results indicate that the DNA walking ACP PCR method of the subject invention can be applied to amplify the unknown sequences upstream or downstream from a known partial cDNA sequence.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Arnold, C., Hodgson, I. J. (1991) Vectorette PCR: a novel approach to genomic walking. PCR Methods Appl. 1:39-42.

Chun, J. Y. (2001) Annealing control primers and its uses. PCT/KR02/01781.

Dominguez, O., Lopez-larrea, C. (1994) Gene walking by unpredictably primed PCR. *Nucleic Acids Res.* 22:3247-3248.

Hwang, I. T., Kim, Y. H., Kim, S. H., Kwak, C. I., Gu, Y. Y., Chun, J. Y. (2003) Annealing control primer system for improving specificity of PCR amplification. *BioTechniques* (in press).

Hwang, I. T., Lee, Y. H., Moon, B. C., Ahn, K. Y., Lee, S. W., Chun, J. Y. (2000) Identification and characterization of a new member of the placental prolactin-like protein-C (PLP-C) subfamily, PLP-Cβ. *Endocrinology* 141:3343-3352.

Iwahana, H., Tsujisawa, T., Katashima, R., Yoshimoto, K., Itakura, M. (1994) PCR with end trimming and cassette ligation: a rapid method to clone exon-intron boundaries and a 5'-upstream sequences of genomic DNA based on a cDNA sequence. *PCR Methods Appl.* 4:19-25.

Jones, D. H., Winistorfer, S. C. (1997) Amplification of 4-9 kb human genomic DNA flanking a known site using a pan-handle PCR variant. *BioTechniques* 23:132-138.

Juretic, N, Theus, M. (1991) Analysis of the polyadenylation consensus sequence context in the genes of nuclear encoded mitochondrial proteins. *FEBS Lett.* 290:4-8.

Kilstrup, M., Kristinansen, K. N. (2000) Rapid genome walking: a simplified oligo-cassette mediated polymerase chain reaction using a single genome-specific primer. *Nucleic Acids Res.* 28:e55.

Lagerstrom, M., Parik, J., Malmgren, H., Stewart, J., Pettersson, U., Landegren, U. (1991) Capture PCR: efficient amplification of DNA fragments adjacent to a known sequence in human and YAC DNA. *PCR Methods Appl.* 1:111-119.

McBratney, S., Sarnow, P. (1996) Evidence for involvement of trans-acting factors in selection of the AUG start codon during eukaryotic translation initiation. *Mol Cell Biol.* 16:3523-3534.

Riley, J., Butler, R., Ogilvie, D., Finnear, R., Jenner, D., Powell, S., Anand, R., Smith, J. C., Markham, A. F. (1990) A novel, rapid method for the isolation of terminal sequences from yeast artificial chromosome (YAC) clones. *Nucleic Acids Res.* 18:2887-2890.

Rosenthal, A., Jones, D. S. C. (1990) Genomic walking and sequencing by oligo-cassette mediated polymerase chain reaction. *Nucleic Acids Res.* 18:3095-3096.

Roux, K. H., Dhanarajan, P. (1990) A strategy for single site PCR amplification of dsDNA: priming digested cloned or genomic DNA from an anchor-modified restriction and a short internal sequence. *BioTechniques* 8:48-57.

Shyamala, V., Ames, G. F. L. (1989) Genome walking by single-specific primer polymerase chain reaction: SSP-PCR. *Gene* 84:1-8.

Siebert, P. D., Chenchik., A., Kellogg., D. E., Lukyanov, K. A., Lukyanov, S. A. (1995) An improved PCR method for walking in uncloned genomic DNA. *Nucleic Acids Res.* 23:1087-1088.

Triglia, T., Peterson, M. G., Kemp, D. J. (1988) A procedure for in vitro amplification of DNA segments that lie outside the boundaries of known sequences. *Nucleic Acids Res.* 16: 8186.

Trueba, G. A., Johnson, R. C. (1996) Random primed genome walking PCR: a simple procedure to retrieve nucleotide fragments adjacent to known DNA sequences. *BioTechniques* 21:20.

Willems, H. (1998) Adaptor PCR for the specific amplification of unknown DNA fragments. *BioTechniques* 24:26-28.

What is claimed is:

1. A method for amplifying an unknown nucleotide sequence adjacent to a known nucleotide sequence, which comprises the step of (a) performing a primary amplification of said unknown nucleotide sequence using a DNA walking annealing control primer (DW-ACP) and a first target-specific primer; in which said step (a) comprises:

(a-1) performing a first-stage amplification of said unknown nucleotide sequence at a first annealing temperature, comprising at least one cycle of primer annealing, primer extending and denaturing using a first degenerate DW-ACP containing a degenerate random nucleotide sequence to hybridize with said unknown nucleotide sequence and a hybridizing nucleotide sequence substantially complementary to a site on said unknown nucleotide sequence, wherein said first annealing temperature enables said first degenerate DW-ACP to function as a primer, the annealing portion of the first DW-ACP is restricted to the portion consisting of said degenerate random nucleotide sequence and hybridizing nucleotide sequence at the first annealing temperature, whereby a first degenerate DW-ACP extension product is generated; and (a-2) performing a second-stage amplification at a second annealing temperature to render said first degenerate DW-ACP not to function as a primer, comprising:

(a-2-1) amplifying said first degenerate DW-ACP extension product using said first target-specific primer to hybridize with a target-specific nucleotide sequence substantially complementary to a site on said known nucleotide sequence, whereby a target-specific primer extension product is generated, (a-2-2) amplifying said target-specific primer extension product using a second DW-ACP to hybridize with a nucleotide sequence complementary to said first degenerate DW-ACP sequence of said target-specific primer extension product, whereby a second DW-ACP extension product is generated, and (a-2-3) amplifying said second DW-ACP extension product using said second DW-ACP and said first target-specific primer, whereby a primary amplification product without a degenerate random nucleotide sequence is generated, wherein said first degenerate DW-ACP has a general formula I:

$$5'\text{-}X_p\text{-}Y_q\text{-}Z_r\text{-}Q_s\text{-}3' \qquad (I)$$

wherein, $X_p$ represents a 5'-end portion having a pre-selected nucleotide sequence, $Y_q$ represents a regulator portion comprising contiguous nucleotides having at least two universal base or non-discriminatory base analog residues, $Z_r$ represents a degenerate random sequence portion having a degenerated random nucleotide sequence, $Q_s$ represents a 3'-end portion having a hybridizing nucleotide sequence substantially complementary to a site on said unknown nucleotide sequence to hybridize therewith, p, q, r and s represent the number of nucleotides, and X, Y, Z and Q are deoxyribonucleotide or ribonucleotide, p represents an integer of 10 to 60, q is at least 3, r represents an integer from 2 to 5, s represents an integer of 3 to 10, and $Y_q$ consists of deoxyinosine or inosine.

2. The method according to claim 1, wherein said first-stage amplification is performed for one cycle.

3. The method according to claim 1, wherein said second-stage amplification is performed for at least 5 cycles.

4. The method according to claim 1, wherein said first annealing temperature is between about 35° C. and 50° C.

5. The method according to claim 1, wherein said second annealing temperature is between about 50° C. and 72° C.

6. The method according to claim 1, wherein said second DW-ACP has a general formula II:

$$5'\text{-}X'_p\text{-}S_u\text{-}Y'_v\text{-}Z'_w\text{-}3' \qquad (II)$$

wherein, $X'_p$ represents a 5'-end portion having a nucleotide sequence corresponding to the 5'-end portion of the first degenerate DW-ACP, $S_u$ represents a supplementary annealing portion comprising a nucleotide sequence to hybridize with a portion opposite to the regulator portion of the first degenerate DW-ACP in the target-specific primer extension product of the step (a-2-1), $Y'_v$ represents a regulator portion comprising at least two universal base or non-discriminatory base analog residues and prevents annealing of said $X'_p$ and $S_u$ portions to non-target sequences except to the nucleotide sequence complementary to the first degenerate DW-ACP, $Z'_w$ represents a 3'-end portion having a nucleotide sequence corresponding to the 3'-end portion of the first degenerate DW-ACP, p, u, v and w represent the number of nucleotides, and X', S, Y', and Z' are deoxyribonucleotide or ribonucleotide.

7. The method according to claim 1, wherein said method further comprises the step of (c) performing a secondary amplification at a third annealing temperature, comprising at least one cycle of primer annealing, primer extending and denaturing, using a third DW-ACP comprising at its 3'-end portion a nucleotide sequence to hybridize with the opposite-sense nucleotide sequence to said second DW-ACP sequence present at the 3'-end of said primary amplification product and said first target-specific primer of the step (a) or a nested target-specific primer designed to amplify an internal region of said primary amplification product.

8. The method according to claim 7, wherein said third annealing temperature ranges from about 50° C. and 72° C.

9. The method according to claim 7, wherein said method further comprises the step (b) of purifying a reaction resultant of the step (a) to remove said first degenerate DW-ACP, said second DW-ACP and said first target-specific primer prior to performing the step (c).

10. The method according to claim 7, wherein said third DW-ACP has a general formula III:

$$5'\text{-}X''_p\text{-}Y''_q\text{-}C_c\text{-}3' \qquad (III)$$

wherein, $X''_p$ represents a 5'-end portion having a nucleotide sequence corresponding to all or a part of the 5'-end portion of said second DW-ACP, $Y''_q$ represents a regulator portion comprising at least two universal base or non-discriminatory base analog residues corresponding to the supplementary annealing portion, a part of the 5'-end portion, a part of supplementary annealing portion plus a part of the 5'-end portion, or a part of supplementary annealing portion plus a part of the regulator portion of the second DW-ACP of the formula II and prevents annealing of said $X''_p$ portion to non-target sequences of said primary amplification product except to the nucleotide sequence complementary to said second DW-ACP, $C_c$ represents a 3'-end portion having a nucleotide sequence to hybridize with the opposite-sense nucleotide sequence to all or a part of the 3'-end portion and regulator portion sequences of said second DW-ACP, p, q and c represent the number of nucleotides, and X", Y", and C are deoxyribonucleotide or ribonucleotide.

11. The method according to claim 1, wherein said nucleotide sequence to be amplified is gDNA or cDNA.

12. The method according to any one of claims 6 and 10, wherein said universal base or non-discriminatory base analog residue is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'0-methoxyethyl nebularine, 2'-0-methoxyethyl 5-nitroindole, 2'-0-methoxyethyl 4-nitro-benzimidazole, 2'-0-methoxyethyl 3-nitropyrrole, and combinations thereof.

13. The method according to 12, wherein said universal base or non-discriminatory base analog residue is deoxyinosine, inosine, 1-(2'-deoxy-beta-D-ribofuranosyl)-3-nitropyrrole or 5-nitroindole.

14. The method according to 13, wherein said universal base or non-discriminatory base analog residue is deoxyinosine.

15. The method according to any one of claims 6 and 10, wherein said regulator portion comprise contiguous nucleotides having universal base or non-discriminatory base analog residue.

16. The method according to any one of claims 6 and 10, wherein p represents an integer of 10 to 60.

17. The method according to any one of claims 6 and 10, wherein q or u is at least 3.

18. The method according to any one of claims 6 and 10, wherein q or u represents an integer of 2 to 10.

19. The method according to claim 6, wherein v represents an integer of 2 to 5.

20. The method according to claim 6, wherein w represents an integer of 3 to 10.

21. The method according to claim 10, wherein c represents an integer of 5 to 15.

22. The method according to claim 6, wherein S comprises at least 2 contiguous deoxyguanosine nucleotides.

23. The method according to claim 10, wherein C comprises at least 2 contiguous deoxyguanosine nucleotides at a site to hybridize with the opposite-sense nucleotide sequence to the regulator portion sequences of said second DW-ACP.

24. A DNA walking annealing control primer for amplifying an unknown nucleotide sequence adjacent to a known nucleotide sequence, which is represented by the following general formula I:

$$5'-X_p-Y_q-Z_r-Q_s-3'\qquad(I)$$

wherein, $X_p$ represents a 5'-end portion having a pre-selected nucleotide sequence, $Y_q$ represents a regulator portion comprising at least two universal base or non-discriminatory base analog residues, $Z_r$ represents a degenerate random sequence portion having a degenerated random nucleotide sequence, $Q_s$ represents a 3'-end portion having a hybridizing nucleotide sequence substantially complementary to a site on said unknown nucleotide sequence to hybridize therewith, p, q, r and s represent the number of nucleotides, and X, Y, Z and Q are deoxyribonucleotide or ribonucleotide.

25. A DNA walking annealing control primer for amplifying an unknown nucleotide sequence adjacent to a known nucleotide sequence, which is represented by the following general formula II:

$$5'-X'_p-S_u-Y'_v-Z'_w-3'\qquad(II)$$

wherein, $X'_p$ represents a 5'-end portion having a nucleotide sequence corresponding to the 5'-end portion of the first degenerate DW-ACP, $S_u$ represents a supplementary annealing portion comprising a nucleotide sequence to hybridize with a portion opposite to the regulator portion of the first degenerate DW-ACP in the target-specific primer extension product of the step (a-2-1), $Y'_v$ represents a regulator portion comprising at least two universal base or non-discriminatory base analog residues and prevents annealing of said $X'_p$ and $S_u$ portions to non-target sequences of the amplified product of the step (a) except to the nucleotide sequence complementary to the first degenerate DW-ACP, $Z'_w$ represents a 3'-end portion having a nucleotide sequence corresponding to the 3'-end portion of the first degenerate DW-ACP, p, u, v and w represent the number of nucleotides, and X', S, Y', and Z' are deoxyribonucleotide or ribonucleotide.

26. A DNA walking annealing control primer for amplifying an unknown nucleotide sequence adjacent to a known nucleotide sequence, which is represented by the following general formula III:

$$5'-X''_p-Y''_q-C_c-3'\qquad(III)$$

wherein, $X''_p$ represents a 5'-end portion having a nucleotide sequence corresponding to all or a part of the 5'-end portion of said second DW-ACP, $Y''_q$ represents a regulator portion comprising at least two universal base or non-discriminatory base analog residues corresponding to the supplementary annealing portion, a part of the 5'-end portion, a part of supplementary annealing portion plus a part of the 5'-end portion, or a part of supplementary annealing portion plus a part of the regulator portion of the second DW-ACP of the formula II and prevents annealing of said $X''_p$ portion to non-target sequences of said primary amplification product except to the nucleotide sequence complementary to said second DW-ACP, $C_c$ represents a 3'-end portion having a nucleotide sequence to hybridize with the opposite-sense nucleotide sequence to all or a part of the 3'-end portion and regulator portion sequences of said second DW-ACP, p, q and c represent the number of nucleotides, and X", Y", and C are deoxyribonucleotide or ribonucleotide.

27. A kit for amplifying an unknown nucleotide sequence adjacent to a known nucleotide sequence, which comprises a primer wherein the primer is selected from the group consisting of:

(a) a DNA walking annealing control primer which is represented by the following general formula I:

$$5'-X_p-Y_q-Z_r-Q_s-3\qquad(I)$$

wherein $X_p$ represents a 5'-end portion having a re-selected nucleotide sequence, $Y_q$ represents a regulator portion comprising at least two universal base or non-discriminatory base analog residues, $Z_r$ represents a degenerate random sequence portion having degenerated random nucleotide sequence, $Q_s$ represents a 3'-end portion having a hybridizing nucleotide sequence substantially complementary to a site on said unknown nucleotide sequence to hybridize therewith, p, q, r and s represent the number of nucleotides, and X, Y, Z and Q are deoxyribonucleotide or ribonucleotide, (b) a DNA walking annealing control primer which is represented by the following general formula II:

$$5'-X'_p-S_u-Y'_v-Z'_w-3'\qquad(II)$$

wherein $X'_p$ represents a 5'-end portion having a nucleotide sequence corresponding to the 5'-end portion of the first degenerate DW-ACP, $S_u$ represents a supplementary annealing portion comprising a nucleotide sequence to hybridize with a portion opposite to the regulator portion of the first degenerate DW-ACP in the target-specific primer extension product of the step (a-2-1), $Y'_v$ represents a regulator portion comprising at least two universal base or non-discriminatory base analog residues and prevents annealing of said $X'_p$ and $S_u$ portions to non-target sequences of the amplified product of the step (a) except to the nucleotide sequence complementary to the first degenerate DW-ACP, $Z'_w$ represents a 3'-end portion having a nucleotide sequence corresponding to the 3'-end portion of the first degenerate DW-ACP, p, u, v and w represent the number of nucleotides, and X', S, Y', and Z' are deoxyribonucleotide or ribonucleotide, (c) a DNA walking annealing control primer which is represented by the following general formula III:

$$5'-X''_p-Y''_q-C_c-3'\qquad(III)$$

wherein $X''_p$ represents a 5'-end portion having a nucleotide sequence corresponding to all or a part of the 5'-end portion of said second DW-ACP, $Y''_q$ represents a regulator portion comprising at least two universal base or non-discriminatory base analog residues corresponding to the supplementary annealing portion, a part of the 5'-end portion, a part of supplementary annealing portion plus a part of the 5'-end portion, or a part of supplementary annealing portion plus a part of the regulator portion of the second DW-ACP of the formula II and prevents annealing of said $X''_p$ portion to non-target sequences of said primary amplification product except to the nucleotide sequence complementary to said second DW-ACP, $C_c$ represents a 3'-end portion having a nucleotide sequence to hybridize with the opposite-sense nucleotide sequence to all or a part of the 3'-end portion and regulator portion sequences of said second DW-ACP, p, q and c represent the number of nucleotides, and X", Y", and C are deoxyribonucleotide or ribonucleotide and (d) combinations thereof.

* * * * *

```
                          SEQUENCE LISTING

<160> NUMBER OF SEQ ID NOS: 28

<210> SEQ ID NO 1
<211> LENGTH: 33
<212> TYPE: DNA
<213> ORGANISM: Artificial Sequence
<220> FEATURE:
<223> OTHER INFORMATION: primer (DW-ACP1-A)
<220> FEATURE:
<221> NAME/KEY: misc_feature
<222> LOCATION: (22)..(28)
<223> OTHER INFORMATION: n denotes deoxyinosine

<400> SEQUENCE: 1
tcacagaagt atgccaagcg annnnnnnag gtc                                33

<210> SEQ ID NO 2
<211> LENGTH: 33
<212> TYPE: DNA
<213> ORGANISM: Artificial Sequence
<220> FEATURE:
<223> OTHER INFORMATION: primer (DW-ACP1-C)
<220> FEATURE:
<221> NAME/KEY: misc_feature
<222> LOCATION: (22)..(28)
<223> OTHER INFORMATION: n denotes deoxyinosine

<400> SEQUENCE: 2
tcacagaagt atgccaagcg annnnnnncg gtc                                33

<210> SEQ ID NO 3
<211> LENGTH: 33
<212> TYPE: DNA
<213> ORGANISM: Artificial Sequence
<220> FEATURE:
<223> OTHER INFORMATION: primer (DW-ACP1-T)
<220> FEATURE:
<221> NAME/KEY: misc_feature
```

```
<222> LOCATION: (22)..(28)
<223> OTHER INFORMATION: n denotes deoxyinosine

<400> SEQUENCE: 3
tcacagaagt atgccaagcg annnnnnntg gtc                                    33

<210> SEQ ID NO 4
<211> LENGTH: 33
<212> TYPE: DNA
<213> ORGANISM: Artificial Sequence
<220> FEATURE:
<223> OTHER INFORMATION: primer (DW-ACP1-G)
<220> FEATURE:
<221> NAME/KEY: misc_feature
<222> LOCATION: (22)..(28)
<223> OTHER INFORMATION: n denotes deoxyinosine

<400> SEQUENCE: 4
tcacagaagt atgccaagcg annnnnnngg gtc                                    33

<210> SEQ ID NO 5
<211> LENGTH: 33
<212> TYPE: DNA
<213> ORGANISM: Artificial Sequence
<220> FEATURE:
<223> OTHER INFORMATION: primer (DW-ACP2-N)
<220> FEATURE:
<221> NAME/KEY: misc_feature
<222> LOCATION: (26)..(29)
<223> OTHER INFORMATION: n denotes deoxyinosine

<400> SEQUENCE: 5
tcacagaagt atgccaagcg aggggnnnng gtc                                    33

<210> SEQ ID NO 6
<211> LENGTH: 33
<212> TYPE: DNA
<213> ORGANISM: Artificial Sequence
<220> FEATURE:
<223> OTHER INFORMATION: primer (DW-ACP2-NA)
<220> FEATURE:
<221> NAME/KEY: misc_feature
<222> LOCATION: (26)..(28)
<223> OTHER INFORMATION: n denotes deoxyinosine

<400> SEQUENCE: 6
tcacagaagt atgccaagcg aggggnnnag gtc                                    33

<210> SEQ ID NO 7
<211> LENGTH: 33
<212> TYPE: DNA
<213> ORGANISM: Artificial Sequence
<220> FEATURE:
<223> OTHER INFORMATION: primer (DW-ACP2-NC)
<220> FEATURE:
<221> NAME/KEY: misc_feature
<222> LOCATION: (26)..(28)
<223> OTHER INFORMATION: n denotes deoxyinosine

<400> SEQUENCE: 7
tcacagaagt atgccaagcg aggggnnncg gtc                                    33

<210> SEQ ID NO 8
<211> LENGTH: 33
<212> TYPE: DNA
<213> ORGANISM: Artificial Sequence
<220> FEATURE:
<223> OTHER INFORMATION: primer (DW-ACP2-NT)
<220> FEATURE:
<221> NAME/KEY: misc_feature
```

<222> LOCATION: (26)..(28)
<223> OTHER INFORMATION: n denotes deoxyinosine

<400> SEQUENCE: 8
tcacagaagt atgccaagcg aggggnnntg gtc                                    33

<210> SEQ ID NO 9
<211> LENGTH: 33
<212> TYPE: DNA
<213> ORGANISM: Artificial Sequence
<220> FEATURE:
<223> OTHER INFORMATION: primer (DW-ACP2-NG)
<220> FEATURE:
<221> NAME/KEY: misc_feature
<222> LOCATION: (26)..(28)
<223> OTHER INFORMATION: n denotes deoxyinosine

<400> SEQUENCE: 9
tcacagaagt atgccaagcg aggggnnngg gtc                                    33

<210> SEQ ID NO 10
<211> LENGTH: 33
<212> TYPE: DNA
<213> ORGANISM: Artificial Sequence
<220> FEATURE:
<223> OTHER INFORMATION: primer (DW-ACP3-N1)
<220> FEATURE:
<221> NAME/KEY: misc_feature
<222> LOCATION: (22)..(25)
<223> OTHER INFORMATION: n denotes deoxyinosine

<400> SEQUENCE: 10
tcacagaagt atgccaagcg annnnggggg gtc                                    33

<210> SEQ ID NO 11
<211> LENGTH: 33
<212> TYPE: DNA
<213> ORGANISM: Artificial Sequence
<220> FEATURE:
<223> OTHER INFORMATION: primer (DW-ACP3-N2)
<220> FEATURE:
<221> NAME/KEY: misc_feature
<222> LOCATION: (23)..(26)
<223> OTHER INFORMATION: n denotes deoxyinosine

<400> SEQUENCE: 11
tcacagaagt atgccaagcg agnnnngggg gtc                                    33

<210> SEQ ID NO 12
<211> LENGTH: 33
<212> TYPE: DNA
<213> ORGANISM: Artificial Sequence
<220> FEATURE:
<223> OTHER INFORMATION: primer (DW-ACP3-N3)
<220> FEATURE:
<221> NAME/KEY: misc_feature
<222> LOCATION: (24)..(27)
<223> OTHER INFORMATION: n denotes deoxyinosine

<400> SEQUENCE: 12
tcacagaagt atgccaagcg aggnnnnggg gtc                                    33

<210> SEQ ID NO 13
<211> LENGTH: 20
<212> TYPE: DNA
<213> ORGANISM: Artificial Sequence
<220> FEATURE:
<223> OTHER INFORMATION: primer (Nested DW-P3-N)

<400> SEQUENCE: 13
ccaagcgagg ggggggggtc                                              20

<210> SEQ ID NO 14
<211> LENGTH: 29
<212> TYPE: DNA
<213> ORGANISM: Artificial Sequence
<220> FEATURE:
<223> OTHER INFORMATION: primer (DW-P1-A)
<220> FEATURE:
<221> NAME/KEY: misc_feature
<222> LOCATION: (22)..(24)
<223> OTHER INFORMATION: n is any base

<400> SEQUENCE: 14
tcacagaagt atgccaagcg annnaggtc                                    29

<210> SEQ ID NO 15
<211> LENGTH: 29
<212> TYPE: DNA
<213> ORGANISM: Artificial Sequence
<220> FEATURE:
<223> OTHER INFORMATION: primer (DW-P1-C)
<220> FEATURE:
<221> NAME/KEY: misc_feature
<222> LOCATION: (22)..(24)
<223> OTHER INFORMATION: n is any base

<400> SEQUENCE: 15
tcacagaagt atgccaagcg annncggtc                                    29

<210> SEQ ID NO 16
<211> LENGTH: 29
<212> TYPE: DNA
<213> ORGANISM: Artificial Sequence
<220> FEATURE:
<223> OTHER INFORMATION: primer (DW-P1-T)
<220> FEATURE:
<221> NAME/KEY: misc_feature
<222> LOCATION: (22)..(24)
<223> OTHER INFORMATION: n is any base

<400> SEQUENCE: 16
tcacagaagt atgccaagcg annntggtc                                    29

<210> SEQ ID NO 17
<211> LENGTH: 29
<212> TYPE: DNA
<213> ORGANISM: Artificial Sequence
<220> FEATURE:
<223> OTHER INFORMATION: primer (DW-P1-G)
<220> FEATURE:
<221> NAME/KEY: misc_feature
<222> LOCATION: (22)..(24)
<223> OTHER INFORMATION: n is any base

<400> SEQUENCE: 17
tcacagaagt atgccaagcg annngggtc                                    29

<210> SEQ ID NO 18
<211> LENGTH: 29
<212> TYPE: DNA
<213> ORGANISM: Artificial Sequence
<220> FEATURE:
<223> OTHER INFORMATION: primer (DW-P1)
<220> FEATURE:
<221> NAME/KEY: misc_feature
<222> LOCATION: (22)..(25)
<223> OTHER INFORMATION: n is any base

<400> SEQUENCE: 18

-continued tcacagaagt atgccaagcg annnnggtc                29

<210> SEQ ID NO 19
<211> LENGTH: 21
<212> TYPE: DNA
<213> ORGANISM: Artificial Sequence
<220> FEATURE:
<223> OTHER INFORMATION: primer (JYC3)

<400> SEQUENCE: 19
tcacagaagt atgccaagcg a                21

<210> SEQ ID NO 20
<211> LENGTH: 20
<212> TYPE: DNA
<213> ORGANISM: Artificial Sequence
<220> FEATURE:
<223> OTHER INFORMATION: primer (mTNFa-C1)

<400> SEQUENCE: 20
caccttgccc tgcccattag                20

<210> SEQ ID NO 21
<211> LENGTH: 22
<212> TYPE: DNA
<213> ORGANISM: Artificial Sequence
<220> FEATURE:
<223> OTHER INFORMATION: primer (mTNFa-C2)

<400> SEQUENCE: 21
ccctcacact gtccttcttg cc                22

<210> SEQ ID NO 22
<211> LENGTH: 23
<212> TYPE: DNA
<213> ORGANISM: Artificial Sequence
<220> FEATURE:
<223> OTHER INFORMATION: primer (mTNFa-C3)

<400> SEQUENCE: 22
gaataagggt tgcccagaca ctc                23

<210> SEQ ID NO 23
<211> LENGTH: 22
<212> TYPE: DNA
<213> ORGANISM: Artificial Sequence
<220> FEATURE:
<223> OTHER INFORMATION: primer (mTNFa-C4)

<400> SEQUENCE: 23
ggagtgcctc ttctgccagt tc                22

<210> SEQ ID NO 24
<211> LENGTH: 22
<212> TYPE: DNA
<213> ORGANISM: Artificial Sequence
<220> FEATURE:
<223> OTHER INFORMATION: primer (mPBP-C1)

<400> SEQUENCE: 24
tccacacctt gaagtcaaag tc                22

<210> SEQ ID NO 25
<211> LENGTH: 24
<212> TYPE: DNA
<213> ORGANISM: Artificial Sequence

```
<220> FEATURE:
<223> OTHER INFORMATION: primer (mPBP-C2)

<400> SEQUENCE: 25
cagaggacag gtactggaca gtag                                          24

<210> SEQ ID NO 26
<211> LENGTH: 23
<212> TYPE: DNA
<213> ORGANISM: Artificial Sequence
<220> FEATURE:
<223> OTHER INFORMATION: primer (mPBP-C3)

<400> SEQUENCE: 26
cagtctcatc accatccagt ctc                                           23

<210> SEQ ID NO 27
<211> LENGTH: 20
<212> TYPE: DNA
<213> ORGANISM: Artificial Sequence
<220> FEATURE:
<223> OTHER INFORMATION: primer (dT20)

<400> SEQUENCE: 27
tttttttttt tttttttttt                                               20

<210> SEQ ID NO 28
<211> LENGTH: 6
<212> TYPE: DNA
<213> ORGANISM: Artificial Sequence
<220> FEATURE:
<223> OTHER INFORMATION: primer (N6)
<220> FEATURE:
<221> NAME/KEY: misc_feature
<222> LOCATION: (1)..(6)
<223> OTHER INFORMATION: n = any base

<400> SEQUENCE: 28 nnnnnn                                                              6
```